(12) United States Patent
Alsberg et al.

(10) Patent No.: US 10,092,654 B2
(45) Date of Patent: Oct. 9, 2018

(54) COACERVATE MICRO AND/OR NANO DROPLETS AND HYDROGELS

(71) Applicant: Case Western Reserve University, Cleveland, OH (US)

(72) Inventors: Eben Alsberg, Cleveland, OH (US); Oju Jeon, Cleveland, OH (US); David Wolfson, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 671 days.

(21) Appl. No.: 14/795,569

(22) Filed: Jul. 9, 2015

(65) Prior Publication Data

US 2016/0008475 A1   Jan. 14, 2016

Related U.S. Application Data

(60) Provisional application No. 62/022,343, filed on Jul. 9, 2014.

(51) Int. Cl.

| | |
|---|---|
| *A01N 63/00* | (2006.01) |
| *A61K 47/36* | (2006.01) |
| *A61K 47/42* | (2017.01) |
| *A61K 31/727* | (2006.01) |
| *A61K 38/18* | (2006.01) |
| *A61K 35/28* | (2015.01) |
| *A61K 9/00* | (2006.01) |
| *A61K 47/00* | (2006.01) |
| *A61L 27/26* | (2006.01) |
| *A61L 27/38* | (2006.01) |
| *A61L 27/52* | (2006.01) |
| *A61L 27/54* | (2006.01) |
| *C12N 5/0775* | (2010.01) |

(52) U.S. Cl.
CPC .............. *A61K 47/36* (2013.01); *A61K 9/00* (2013.01); *A61K 31/727* (2013.01); *A61K 35/28* (2013.01); *A61K 38/1875* (2013.01); *A61K 47/00* (2013.01); *A61K 47/42* (2013.01); *A61L 27/26* (2013.01); *A61L 27/38* (2013.01); *A61L 27/3834* (2013.01); *A61L 27/52* (2013.01); *A61L 27/54* (2013.01); *C12N 5/0662* (2013.01); *A61L 2300/414* (2013.01); *A61L 2430/02* (2013.01); *C12N 2533/54* (2013.01); *C12N 2533/74* (2013.01); *C12N 2537/00* (2013.01); *C12N 2537/10* (2013.01)

(58) Field of Classification Search
CPC .............. A61L 27/25; A61L 2300/414; A61L 2430/02; A61L 27/38; A61L 27/3834; A61L 27/52; A61L 27/54; C08L 5/04; C08L 89/06; A61K 31/727; A61K 35/28; A61K 38/1875; A61K 47/00; A61K 47/36; A61K 47/42; A61K 9/00; C12N 2533/54; C12N 2533/74; C12N 2537/00; C12N 2537/10; C12N 5/00; C12N 5/0662
See application file for complete search history.

(56) References Cited

U.S. PATENT DOCUMENTS 6,916,490 B1   7/2005   Garver et al.

OTHER PUBLICATIONS

Jeon et al. Biomaterials (2009) 30: 2724-2734 (Year: 2009).*
Gao et al. Polymer Degradation and Stability (2009) 94: 1405-1410 (Year: 2009).*
Balakrishnan et al. Biomaterials (2005) 26: 6335-6342 (Year: 2005).*
Nichol et al. Biomaterials (2010) 31: 5536-5544 (Year: 2010).*

* cited by examiner

*Primary Examiner* — Susan M Hanley
(74) *Attorney, Agent, or Firm* — Tarolli, Sundheim, Covell & Tummino LLP

(57) ABSTRACT

A composition includes a plurality of coacervate micro and/or nanodroplets of oxidized alginate and a methacrylated gelatin.

18 Claims, 13 Drawing Sheets

Specification includes a Sequence Listing.

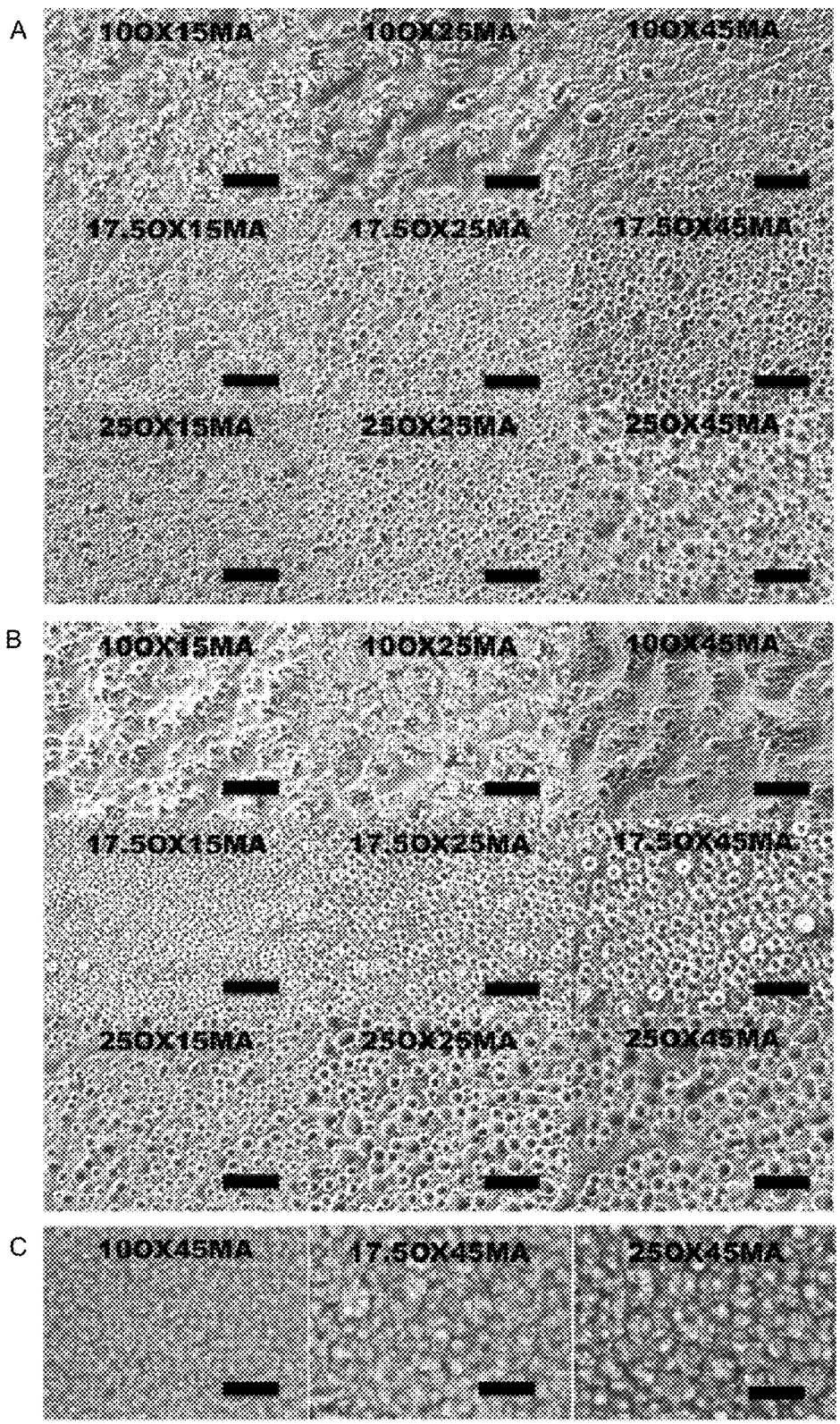
Figs. 3A-C

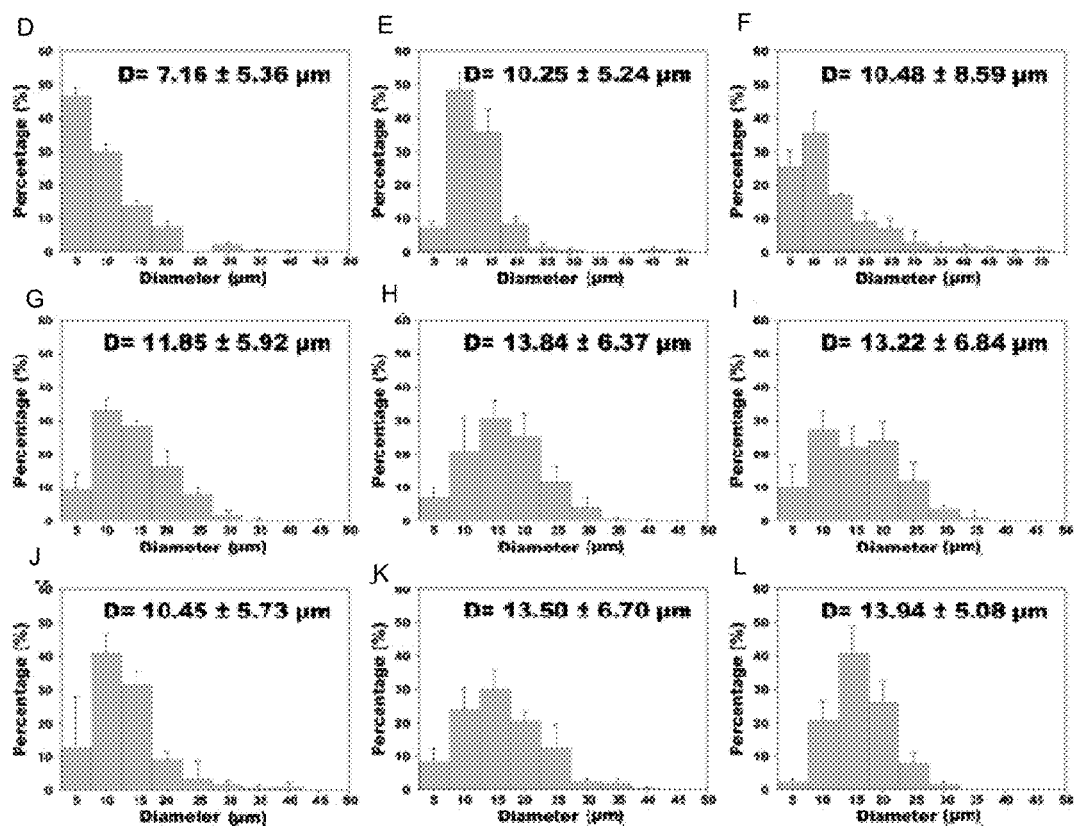
Figs. 3D-L

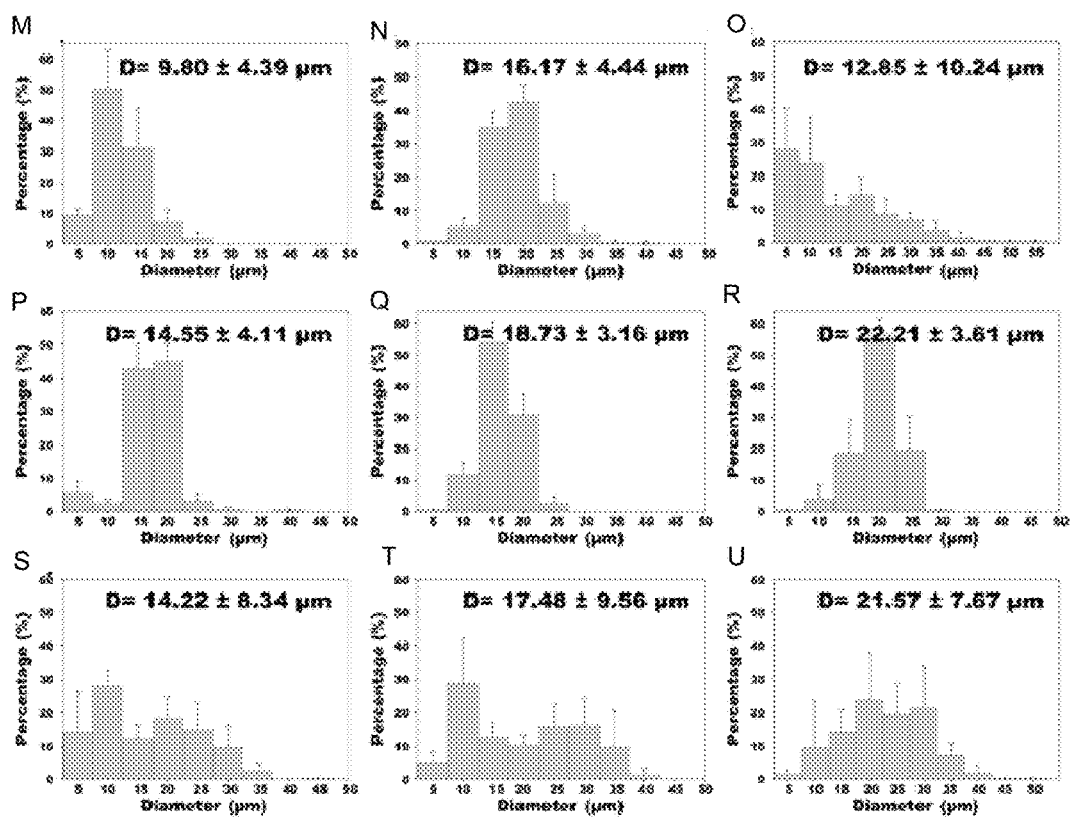
Figs. 3M-U

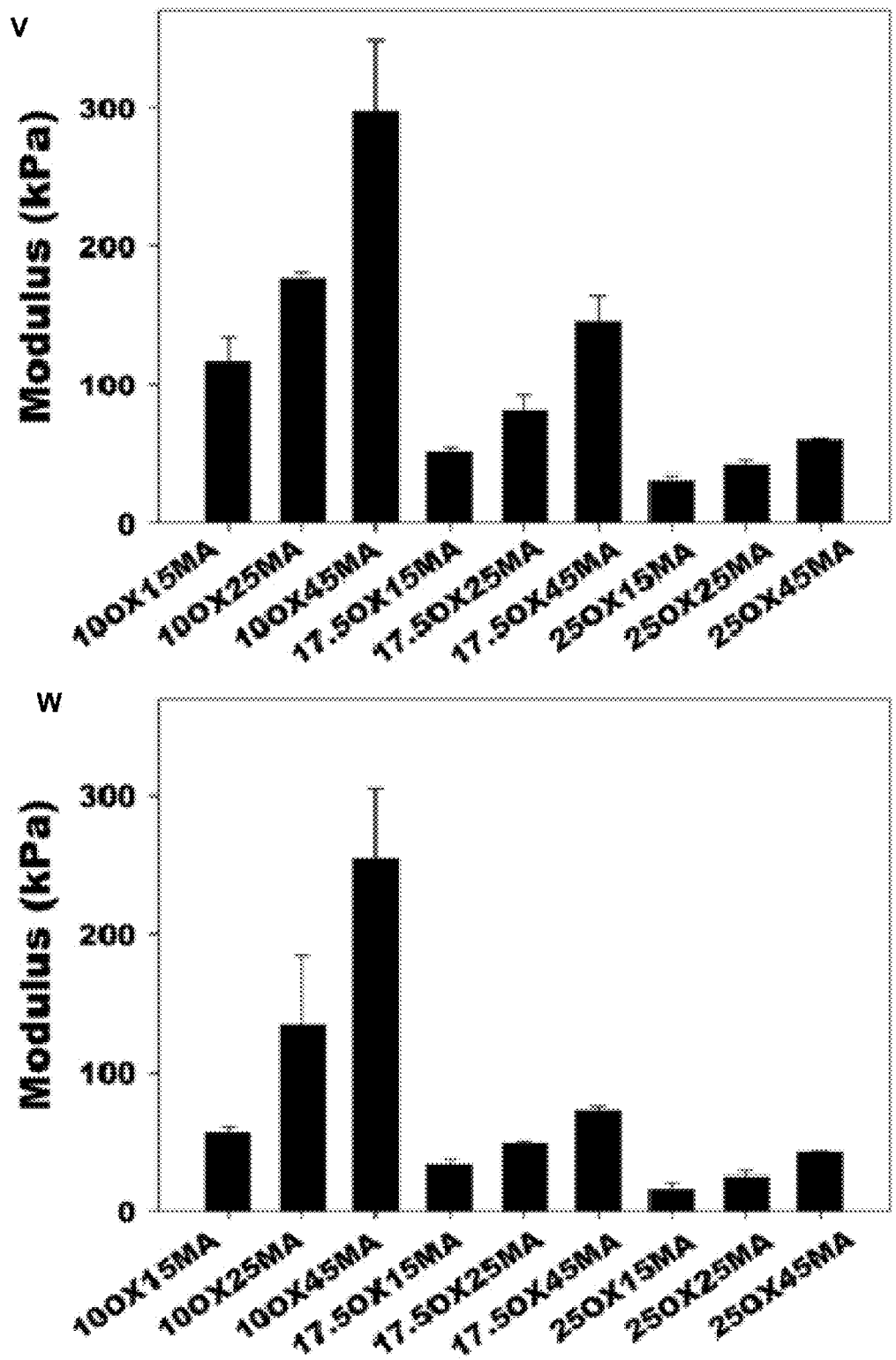
Figs. 3V-W

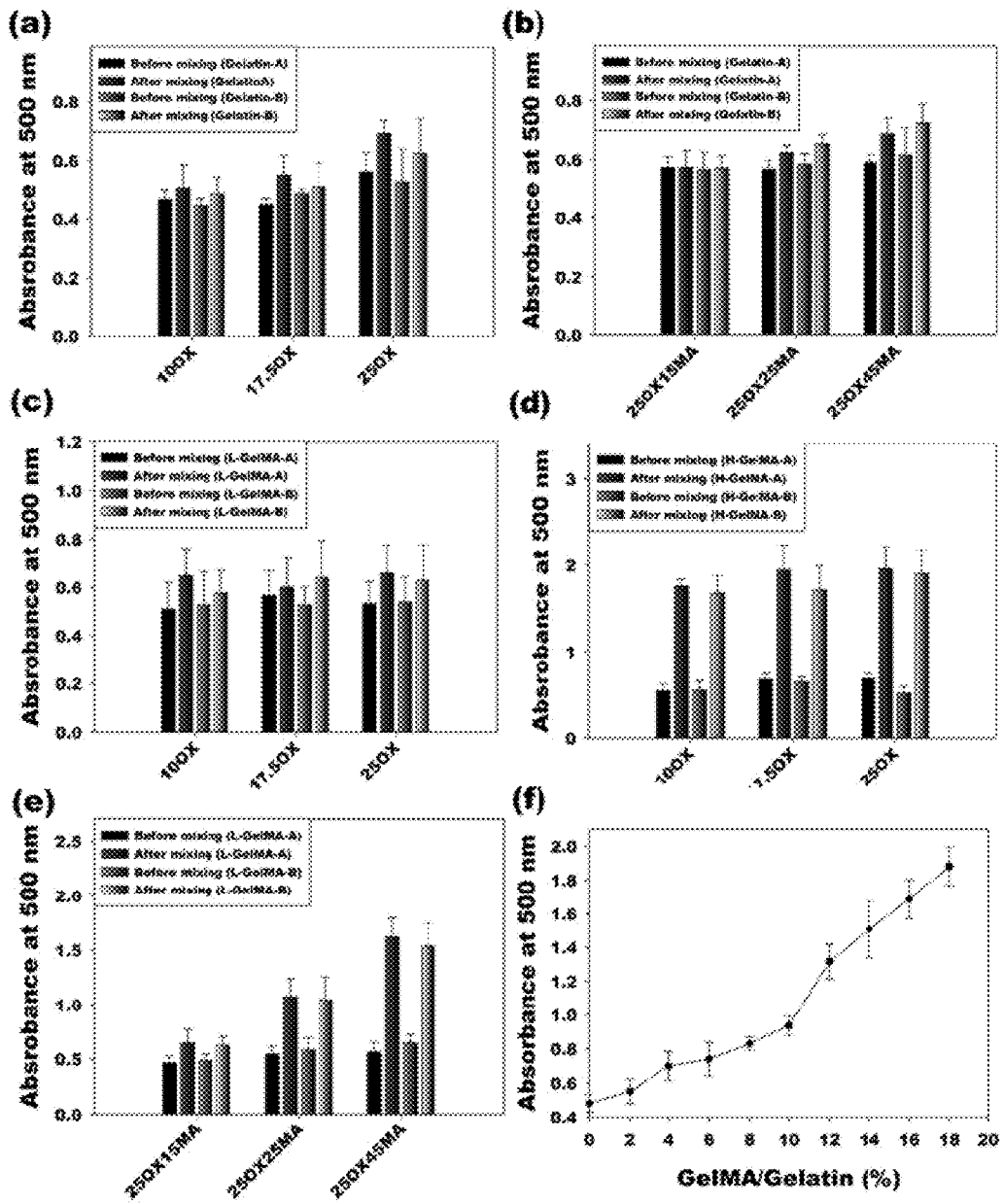
Figs. 4A-F

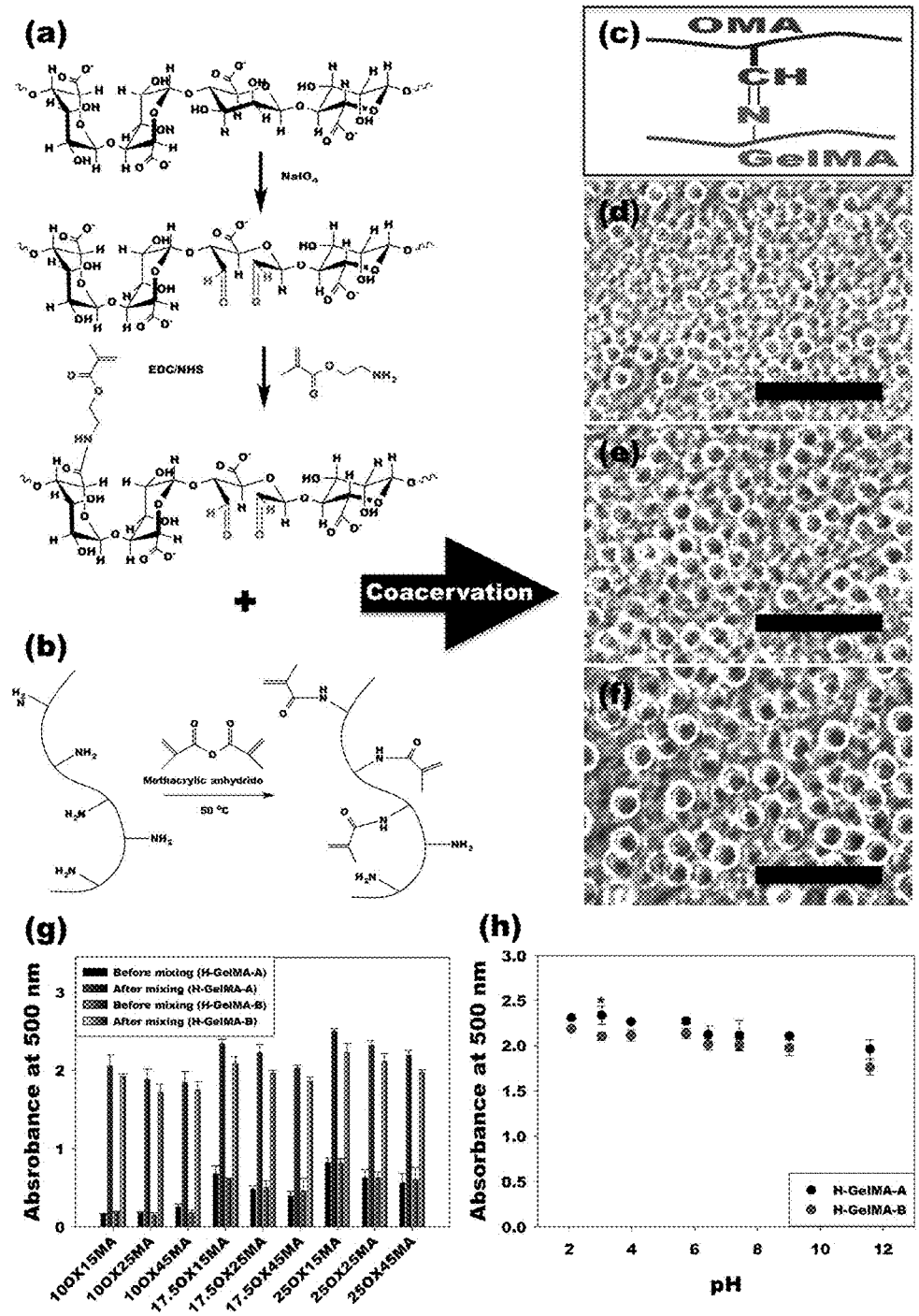
Figs. 8A-H

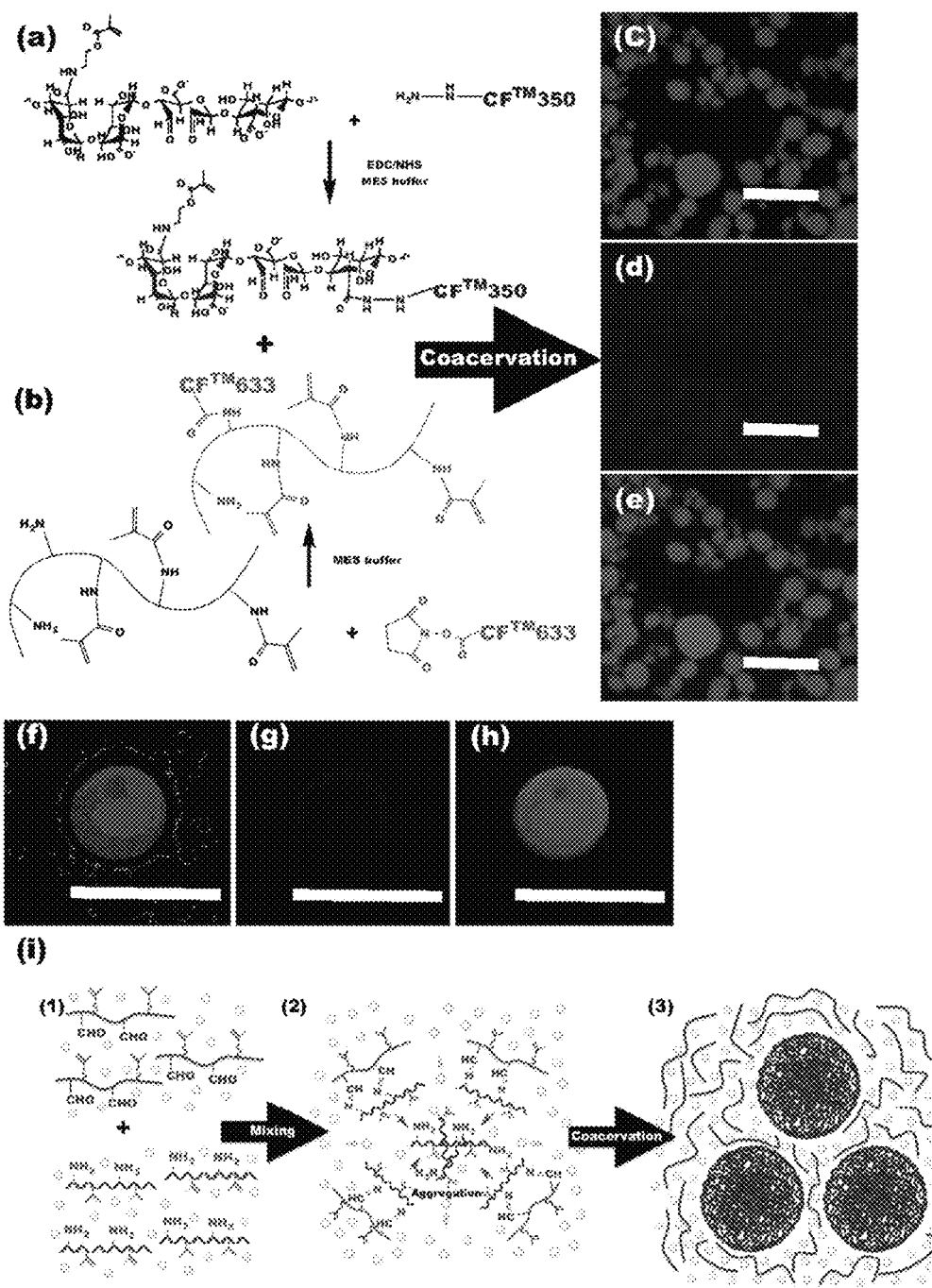
Figs. 9A-I

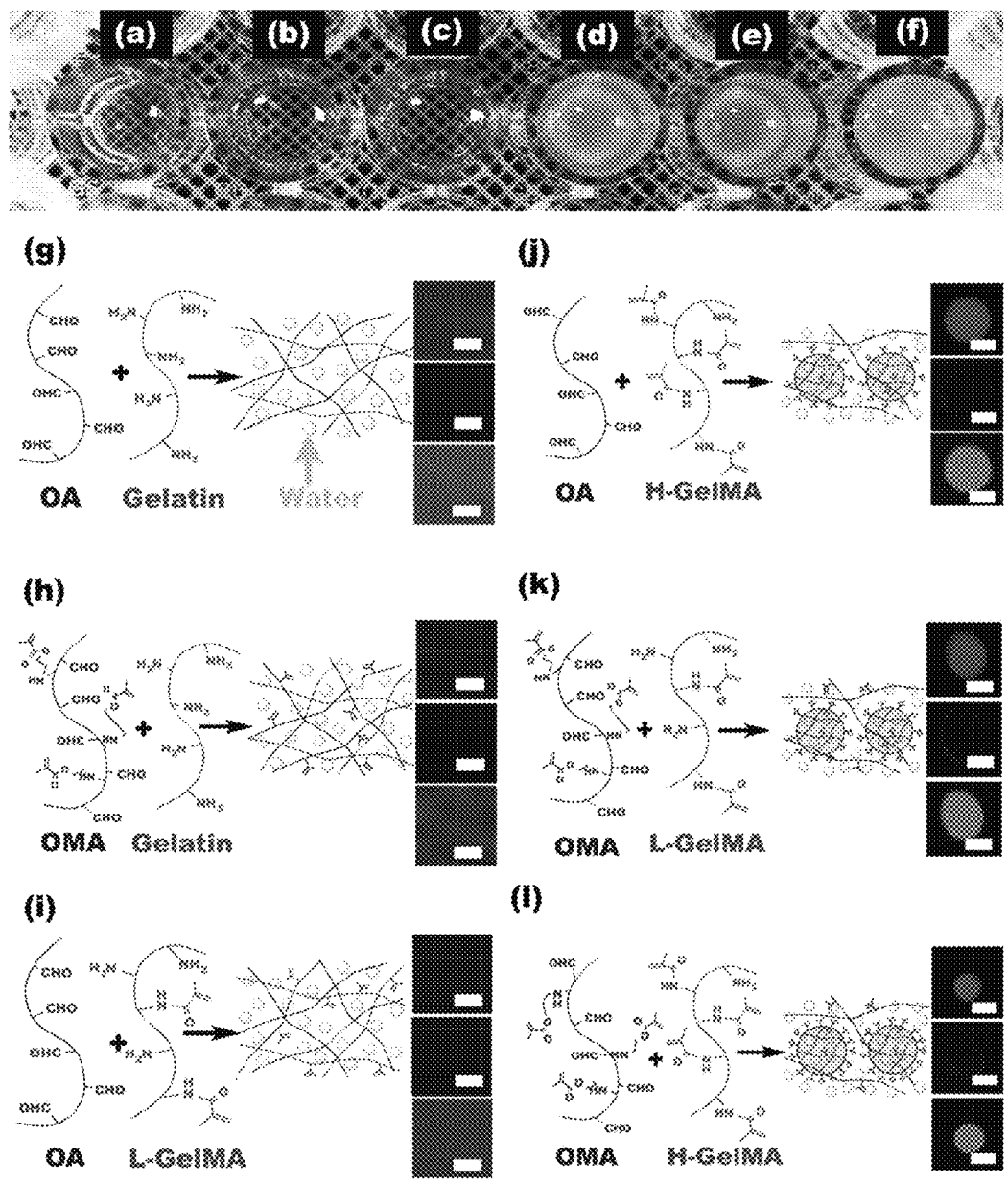
Figs. 10A-L

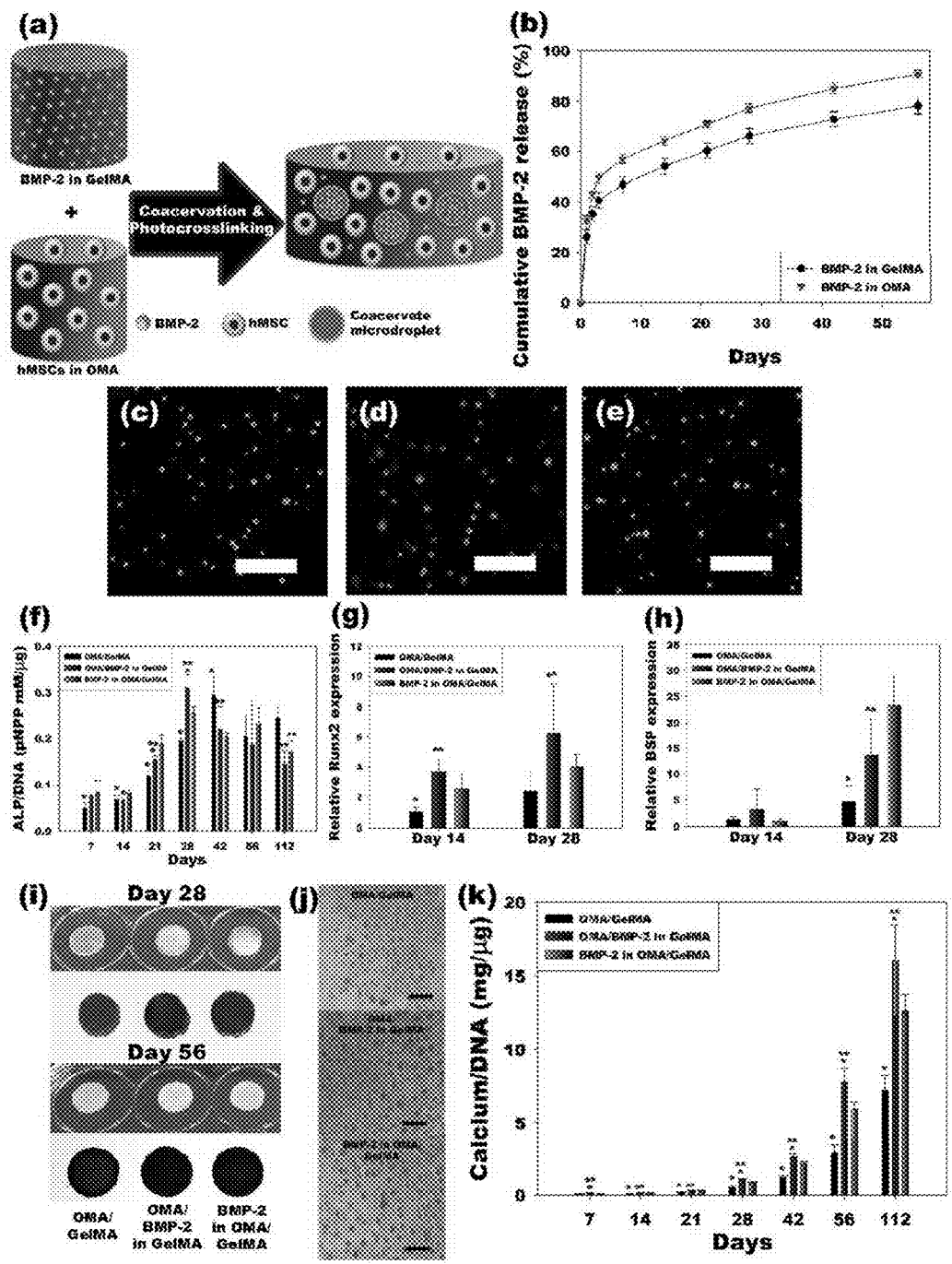
Figs. 11A-K

SEQUENCE LISTING

```
<160> NUMBER OF SEQ ID NOS: 3

<210> SEQ ID NO 1
<211> LENGTH: 40
<212> TYPE: PRT
<213> ORGANISM: Homo sapiens

<400> SEQUENCE: 1

Gly Gly Gly Gly Cys Thr Gly Gly Cys Ala Thr Thr Gly Cys Cys Cys
1               5                   10                  15

Thr Cys Ala Ala Gly Gly Cys Thr Gly Gly Thr Gly Gly Thr Cys Cys
            20                  25                  30

Ala Gly Gly Gly Gly Thr Cys Thr
        35                  40

<210> SEQ ID NO 2
<211> LENGTH: 43
<212> TYPE: PRT
<213> ORGANISM: Homo sapiens

<400> SEQUENCE: 2

Ala Cys Ala Gly Ala Ala Cys Cys Ala Cys Ala Ala Gly Thr Cys Gly
1               5                   10                  15

Gly Thr Gly Cys Ala Ala Thr Gly Gly Cys Thr Gly Gly Thr Ala Gly
            20                  25                  30

Thr Gly Ala Cys Cys Thr Gly Cys Gly Gly Ala
        35                  40

<210> SEQ ID NO 3
<211> LENGTH: 44
<212> TYPE: PRT
<213> ORGANISM: Homo sapiens

<400> SEQUENCE: 3

Ala Cys Cys Cys Thr Ala Ala Cys Cys Cys Thr Gly Gly Ala Gly Ala
1               5                   10                  15

Gly Cys Cys Cys Cys Thr Thr Cys Gly Cys Cys Thr Thr Gly Ala Gly
            20                  25                  30

Ala Thr Ala Thr Cys Gly Gly Gly Gly Gly Cys Ala
        35                  40
```

COACERVATE MICRO AND/OR NANO DROPLETS AND HYDROGELS

RELATED APPLICATION

This application claims priority from U.S. Provisional Application No. 62/022,343, filed Jul. 9, 2014, the subject matter, which is incorporated herein by reference in its entirety.

GOVERNMENT FUNDING

This invention was made with government support under Grant No. AR063194, AR061265, DE023376, and AR007505 awarded by The National Institutes of Health (NIH). The United States government has certain rights in the invention.

BACKGROUND

Complex coacervation is known as liquid-liquid phase separation in aqueous solution by spontaneous aggregation associated with electrostatic matching between two oppositely charged polyelectrolytes. Complex coacervates have been used for direct complexation between bioactive molecules and polysaccharides, micro- or nanoencapsulation of bioactive molecules or cells, and surface coating of particles, due to their unique physicochemical characteristics that can be easily modulated by pH, ionic strength, charge density, and stoichiometry of interacting molecules. However, these systems often require cytotoxic surfactants and/or expensive equipment. The ability to cheaply form cytocompatible coacervates under mild conditions that permit the compartmentalized encapsulation of cells and bioactive factors via simple mixing would be valuable for tissue engineering strategies as it would allow for control over their spatial distribution. However, no coacervate system has been reported capable of simultaneous cell encapsulation and the formation of drug-laden microdroplets under physiological conditions that could be used as a three-dimensional biomaterial for cell encapsulation and transplantation, and tissue engineering applications, due to the harsh physicochemical conditions [i.e., low pH (<4) and high temperature (~60° C.)] typically required for complex coacervation formation.

SUMMARY

Embodiments described herein relate to a complex cytocompatible coacervate system that can be used to form coacervate micro and/or nanodroplets and/or coacevate-laden hydrogels (i.e., coacevate hydrogels). The coacervate micro and/or nanodroplets and/or hydrogels can provide localized, sustained, and/or controlled release of bioactive agents, such as polypeptides and polynucleotides, to cells in or about the coacervate micro and/or nanodroplets and/or hydrogels under physiological conditions in a spatial and/or temporally controlled or predetermined manner.

In some embodiments, a composition can be provided that includes a plurality of coacervate micro and/or nanodroplets. The coacervate micro and/or nanodroplets can include oxidized alginate, a methacrylated gelatin. At least one bioactive agent can be incorporated in the micro and/or nanodroplets. The oxidized alginate can have an oxidation percentage up to about 50%, for example, about 1% to about 50% or about 5% to about 25%. The oxidized alginate can also be methacrylated and have a methacrylation percentage up to about 75%, for example, about 5% to about 45%. The methacrylated gelatin can have a methacrylation percentage, up to about 100%, for example, about 5% to about 99%. In some embodiments, the methacrylated gelatin can have a methacrylation percentage of at least about 10%, for example, at least about 75%.

In some embodiment, the composition can include a cytocompatible hydrogel matrix in which the coacervate micro and/or nanodroplets are suspended. The hydrogel matrix can include cross-linked oxidized methacrylated alginate.

In still other embodiments, the composition can include a plurality of cells that are suspended in the hydrogel matrix. The plurality of coacervate micro and/or nanodroplets can provide controlled release of the bioactive agent to the plurality of cells suspended or provided in the matrix. For example, BMP-2 loaded coacervate micro and/or nanodroplets can be used to provide controlled release of BMP-2 to progenitor cells, such as hMSCs, suspended in the hydrogel matrix.

Other embodiments relate to a hydrogel comprising a crosslinked oxidized alginate and a methacrylated gelatin that form or provide a hydrogel matrix and a plurality of coacervate micro and/or nanodroplets. The hydrogel can include at least one bioactive agent incorporated in the micro and/or nanodroplets and/or matrix. The oxidized alginate can have an oxidation percentage up to about 50%, for example, about 1% to about 50% or about 5% to about 25%. The oxidized alginate can also be methacrylated and have a methacrylation percentage up to about 75%, for example, about 5% to about 45%. The methacrylated gelatin can have a methacrylation percentage, up to about 100%, for example, about 5% to about 99%. In some embodiments, the methacrylated gelatin can have a methacrylation percentage of at least about 10%, for example, at least about 75%. In some embodiments, a plurality of cells is incorporated or provided in the hydrogel matrix and the plurality of coacervate micro and/or nanodroplets can provide controlled release of the bioactive agent to the plurality of cells.

BRIEF DESCRIPTION OF THE DRAWINGS

FIGS. 3(A-W) illustrate images and graphs showing characterization of OMA/GelMA coacervates. (A-B), OMA/GelMA coacervate microdroplets formed by 20 w/v % OMA with various degrees of oxidation and methacrylation and (A) 20 w/v % H-GelMA-A or (B) 20 w/v % H-GelMA-B in PBS at pH 7.4. (C) Photocrosslinked OMA/H-GelMA-B coacervate microdroplet-laden hydrogels. The scale bars indicate 100 μm. Size distribution of OMA/GelMA coacervate microdroplets formed with (d) 10OX15MA/H-GelMA-A, (E) 10OX25MA/H-GelMA-A, (F) 10OX45MA/H-GelMA-A, (G) 17.5OX15MA/H-GelMA-A, (H) 17.5OX25MA/H-GelMA-A, (I) 17.5OX45MA/H-GelMA- A, (J) 25OX15MA/H-GelMA-A, (K) 25OX25MA/H-GelMA-A, (L) 25OX45MA/H-GelMA-A, (M) 10OX15MA/H-GelMA-B, (N) 10OX25MA/H-GelMA-B, (O) 10OX45MA/H-GelMA-B, (P) 17.5OX15MA/H-GelMA-B, (Q) 17.5OX25MA/H-GelMA-B, (R) 17.5OX45MA/H-GelMA-B, (S) 25OX15MA/H-GelMA-B, (T) 25OX25MA/H-GelMA-B and (U) 25OX45MA/H-GelMA-B. The coacervate microdroplet diameters were measured using NIH ImageJ analysis software (n>400 per group). Elastic moduli in compression of OMA/GelMA coacervate microdroplet-laden hydrogels formed with (V) H-GelMA-A and (W) H-GelMA-B.

FIGS. 4(A-F) illustrate graphs showing turbidity of (A) OAs and gelatins, (B) OMAs and gelatins, (C) OAs and L-GelMAs, (D) OAs and H-GelMAs, (E) OMAs and L-GelMAs, and (F) OA and H-GelMA-A/gelatin-A before and after mixing by absorbance measurement at 500 nm to evaluate the degrees of complex coacervate formation.

FIGS. 8(A-H) illustrate the formation of OMA/GelMA coacervates. (A-B), Schematic illustrations of preparation and chemical structures of (A) OMA and (B) GelMA. (C) Schematic illustration of Schiff base reaction between the aldehyde group of the OMA and amine group of the GelMA. (D-F), Representative optical photomicrographs of OMA/GelMA coacervate microdroplets formed by (D) 17.5OX15MA and H-GelMA-B, (E) 17.5OX25MA and H-GelMA-B, and (F) 17.5OX45MA and H-GelMA-B. The scale bars indicate 100 μm. (G) Turbidity of OMA/GelMA solutions prepared at pH 7.4 before and after mixing of two solutions by the measurement of the absorbance at 500 nm to evaluate the degrees of complex coacervate formation. (H) Turbidity of OMA (25OX45MA)/H-GelMA coacervate as a function of pH. All quantitative data is expressed as mean±standard deviation (N=3). Statistical analysis was performed with one-way analysis of variance (ANOVA) with Tukey significant difference post hoc test using Origin software (OriginLab Co). The absorbance of all groups significantly increased after mixing (p<0.001). *p<0.05 compared with H-GelMA-B at a specific pH.

FIGS. 9(A-I) illustrate microstructural characterization of OMA/GelMA coacervates. (A-B), Schematic illustrations for synthesis of fluorescently-labeled (A) 17.5OX15MA and (B) H-GelMA-A. (C-E), Representative fluorescence photomicrographs of OMA/GelMA coacervates. (C) Red channel, (D) blue channel and (E) merged image. (F-H), Representative fluorescence photomicrographs of individual OMA/GelMA coacervate microdroplet with high magnification. (F) Red channel, (G) blue channel and (H) merged image. The scale bars indicate 50 μm. (I) Schematic representation of the formation of OMA/GelMA coacervate microdroplets.

FIGS. 10(A-L) illustrate the effect of alginate and gelatin methacrylation on coacervate formation. (A-F), Representative photograph of (A) OA/Gelatin, (B) OMA/Gelatin, (C) OA/L-GelMA, (D) OA/H-GelMA, (E) OMA/L-GelMA and (F) OMA/H-GelMA mixtures in a 96-well plate. (G-H), Schematic microstructure and representative fluorescence images [red channel (top), blue channel (middle), and merged image (bottom)] of (G) OA/Gelatin, (H) OMA/Gelatin, (I) OA/L-GelMA, (J) OA/H-GelMA, (K) OMA/L-GelMA and (L) OMA/H-GelMA mixtures. The scale bars indicate 30 μm.

FIGS. 11(A-K) illustrate photoencapsulation of hMSCs and BMP-2 in OMA/GelMA coacervate hydrogels induces hMSC osteogenesis. (A) Schematic illustration of in situ formation of BMP-2-loaded coacervate microdroplets-embedded hydrogel for osteogenic differentiation of photoencapsulated hMSC. (B) Release profiles of BMP-2 from photocrosslinked OMA/BMP-2 in GelMA and BMP-2 in OMA/GelMA coacervate microdroplet-laden hydrogels (N=5). (C-E), Live/Dead staining of encapsulated hMSCs in photocrosslinked (C) OMA/GelMA, (D) OMA/BMP-2 in GelMA and (E) BMP-2 in OMA/GelMA coacervate microdroplet-laden hydrogels after 28 days culture in osteogenic differentiation media. (F-H), Quantification of (F) ALP/DNA (N=6), and (G) relative Runx2 (N=6) and (h) BSP (N=6) gene expression in hMSCs encapsulated within hydrogels. (I-K), Mineralization of cell-hydrogel constructs analyzed by (I and J) Alizarin red staining and (J) quantification of calcium content (N=6) in the constructs. The scale bars indicate 100 μm. All quantitative data is expressed as mean±standard deviation. Statistical analysis was performed with one-way analysis of variance (ANOVA) with Tukey significant difference post hoc test using Origin software. *p<0.05 compared with BMP-2 in OMA/GelMA group at a specific time point. **p<0.05 compared with OMA/GelMA group at a specific time point.

DETAILED DESCRIPTION

Figure 1:
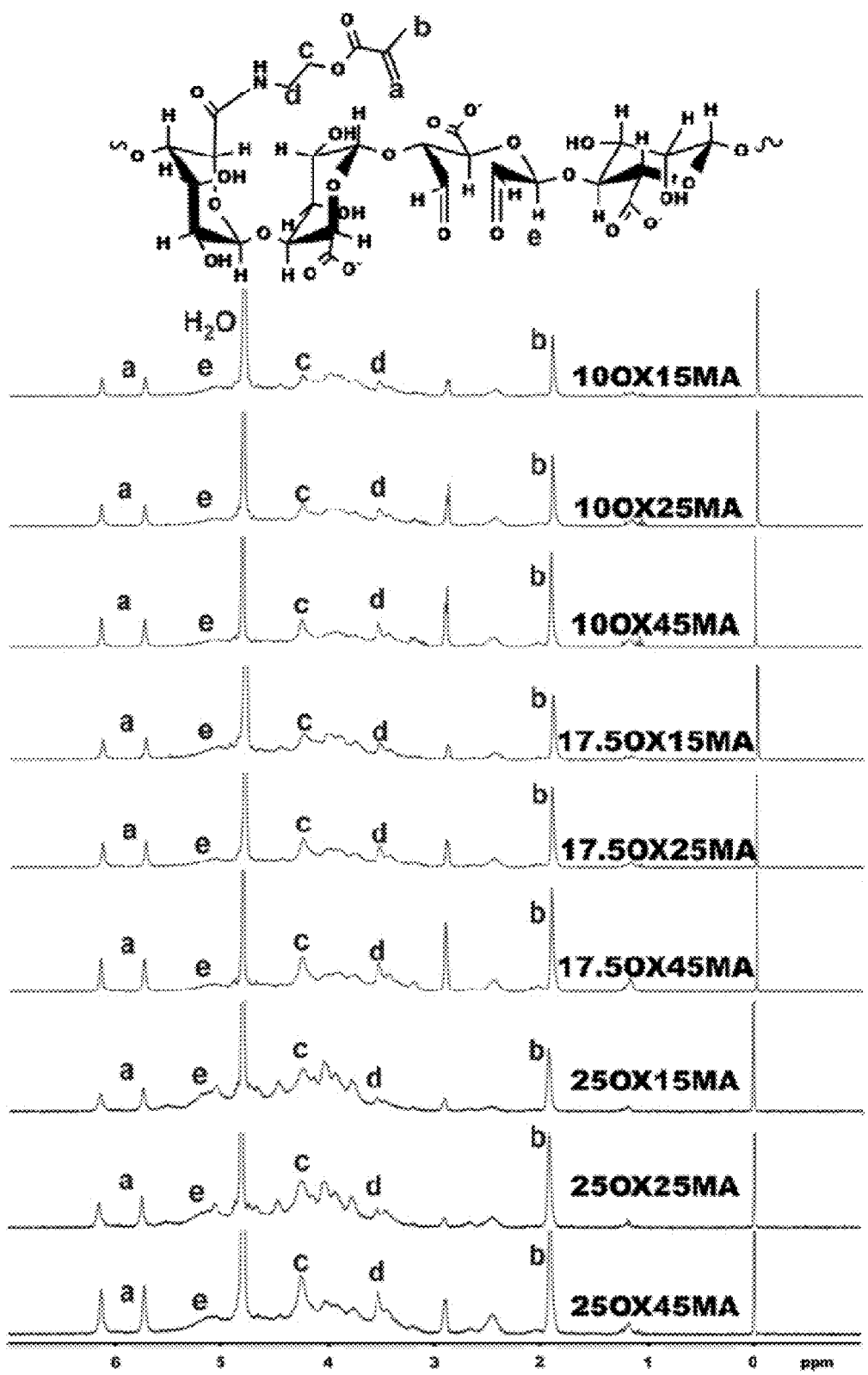
FIG. 1 illustrates $^1$H-NMR spectra of OMAs with various degrees of oxidation and methacrylation in $D_2O$. The OMAs were dissolved in $D_2O$ (2 w/v %), and $^1$H-NMR spectra were recorded on a Varian Unity-300 (300 MHz) NMR spectrometer (Varian Inc.) using 3-(trimethylsilyl)propionic acid-$d_4$ sodium salt (0.05 w/v %) as an internal standard.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarily, or, for example, in the case of binding to DNA duplexes, through specific interactions in the major groove of the double helix.

The term "bioactive agent" refers to any agent capable of promoting tissue formation, destruction, and/or targeting a specific disease state (e.g., cancer). When administered to a host, both human and animal, e.g., the bioactive agent may be used as part of a prophylatic or therapeutic treatment. Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-β I-III)), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, oligonucleotides, proteoglycans, glycoproteins, glycosaminoglycans, and DNA encoding for shRNA. In addition, biological entities, such as viruses, virenos, and prions are considered bioactive agents. The bioactive agents may be water-soluble or water-insoluble and may include those having a high molecular weight, such as proteins, peptides, carbohydrates and glycoproteins.

The term "biocompatibility" or "biocompatible" when used in relation to coacervates described herein refers to coacervates that are neither themselves toxic to the host (e.g., an animal or human), nor degrade (if at all) at a rate that produces byproducts at toxic concentrations in the host. To determine whether any subject coacervates are biocompatible, it may be necessary to conduct a toxicity analysis. Such assays are well known in the art.

The term "biodegradable" refers to those embodiments in which coacervates or hydrogels described herein are intended to degrade during use. In general, degradation attributable to biodegradability involves the degradation of a coacervate or hydrogel into its constituents and encapsulated materials. The degradation rate of a biodegradable coacervate or hydrogel often depends in part on a variety of factors, including the identity of any constituents that form the coacervate and hydrogel and their ratio, the identity and loading of any material (including bioactive agent encapsulated in a coacervate), how any coacervate may be crosslinked and to what extent. For example, a coacervate that is crosslinked will, in all likelihood, degrade more slowly than one that is not crosslinked.

The term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Exemplary progenitor cells can be selected from, but not restricted to, totipotent stem cells, pluripotent stem cells, multipotent stem cells, mesenchymal stem cells (MSCs), hematopoietic stem cells, neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells are selected from, but not restricted to, de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

When used with respect to the bioactive agent, the term "controlled release" is intended to mean that the bioactive agent is released over time in contrast to a bolus type administration in which the entire amount of the bioactive agent is presented to the target at one time. The release will vary as explained below.

The term "gene" or "recombinant gene" refers to a nucleic acid comprising an open reading frame encoding a polypeptide, including both exonic and (optionally) intronic sequences.

The term "gene construct" refers to a vector, plasmid, viral genome or the like which includes an "coding sequence" for a polypeptide or which is otherwise transcribable to a biologically active RNA (e.g., antisense, decoy, ribozyme, etc), can transfect cells, preferably mammalian cells, and can cause expression of the coding sequence in cells transfected with the construct. The gene construct may include one or more regulatory elements operably linked to the coding sequence, as well as intronic sequences, poly adenylation sites, origins of replication, marker genes, etc.

The term "host cell" or "target cell" refers to a cell transduced with a specified transfer vector. The cell is optionally selected from in vitro cells such as those derived from cell culture, ex vivo cells, such as those derived from an organism, and in vivo cells, such as those in an organism.

The term "incorporated" or "encapsulation," when used in reference to a bioactive agent or other material and a coacervate, denotes formulating a bioactive agent or other material into a coacervate useful for controlled release of such agent or material. As used herein, those terms contemplate any manner by which a bioactive agent is incorporated into a coacervate, including for example: distributed throughout the matrix, appended to the surface of microdroplets, and encapsulated inside the matrix or microdroplets. The term "coincorporation" or "coencapsulation" as used herein refers to the incorporation of a bioactive agent in a coacervate and at least another bioactive agent or other material.

The term "microspheres", "microdroplets", "nanospheres", "nanodroplets", or "micro and/or nanodroplets" are used interchangeably and refer to substantially spherical structures formed by a coacervation process. The micro and/or nanodroplets generally have a matrix-type structure, and can incorporate and/or encapsulate a bioactive agent within the matrix. The micro and/or nanodroplets generally have a size distribution within the range of from about 10 nM to about 100 μM. In certain embodiments, over 90% of the microdroplets formed in a single preparation of coacervates have a diameter in excess of about 5 μM. Other sizes are also contemplated herein When a large number of micro and/or nanodroplets are formed in a coacervate composition, they may have a variable size. In certain embodiments, the size distribution may be uniform, e.g., within less than about a 20% standard deviation of the median volume diameter, and in other embodiments, still more uniform or within about 10% of the median volume diameter.

The term "modulation" refers to both up regulation (i.e., activation or stimulation) and down regulation (i.e., inhibition or suppression) of a response.

The term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides. Exemplary nucleic acids for use in the subject invention include antisense, decoy molecules, recombinant genes (including transgenes) and the like.

The phrases "parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal and intrasternal injection and infusion.

The phrase "pharmaceutically acceptable" refers to those coacervates and dosages thereof within the scope of sound medical judgment, suitable for use in contact with the tissues of human beings and animals without excessive toxicity, irritation, allergic response, or other problem or complication, commensurate with a reasonable benefit/risk ratio.

The term "prophylactic or therapeutic" treatment refers to administration to the host of the subject micro and/or nanodroplets. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish or ameliorate the existing unwanted condition or side effects therefrom).

The terms "protein," "polypeptide" and "peptide" are used interchangeably when referring to a gene product.

"Recombinant host cells" refers to cells which have been transformed or transfected with vectors constructed using recombinant DNA techniques.

The terms "recombinant protein," "heterologous protein" and "exogenous protein" are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, the term "subject" can refer to any animal, including, but not limited to, humans and non-human animals (e.g., rodents, arthropods, insects, fish (e.g., zebrafish), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

The phrases "systemic administration," "administered systematically," "peripheral administration" and "administered peripherally" mean the administration of a subject supplement, composition, therapeutic or other material such that it enters the patient's system and, thus, is subject to metabolism and other like processes, for example, subcutaneous administration.

The phrase "therapeutically effective amount" means that amount of a bioactive agent that, when present in a coacervate, produces some desired effect at a reasonable benefit/risk ratio applicable to any medical treatment. In certain embodiments, a therapeutically effective amount of a bioactive agent for in vivo use will likely depend on a number of factors, including: the rate of release of the bioactive agent from the coacervate, which will depend in part on the chemical and physical characteristics of the such coacervate, the identity of the bioactive agent, the mode and method of administration; any other materials incorporated in the coacervate in addition to the bioactive agent.

The term "treating" as used herein is intended to encompass curing as well as ameliorating at least one symptom of any condition or disease.

Embodiments described herein relate to a complex cytocompatible coacervate system that can be used to form coacervate micro and/or nanodroplets and/or coacervate-laden hydrogels (i.e., coacervate hydrogels). The coacervate micro and/or nanodroplets and/or hydrogels can provide localized, sustained, and/or controlled release of bioactive agents, such as polypeptides and polynucleotides, to cells in or about the coacervate micro and/or nanodroplets and/or hydrogels under physiological conditions in a spatial and/or temporally controlled or predetermined manner.

It was found that coacervate micro and/or nanodroplets and/or coacervate-laden hydrogels can be formed under physiological conditions from the simple mixing of photocrosslinkable oxidized alginate (OA) or oxidized, methacrylated alginate (OMA) with methacrylated gelatin (GelMA) at a wide pH range and room temperature. This system enables simultaneous creation of bioactive-laden micro and/or nanodroplets and encapsulation of cells in photopolymerized coacervate hydrogels under physiological conditions. The coacervate system can be utilized as a platform for in situ formation of three-dimensional biomaterials for cell encapsulation and transplantation as well as localized, sustained, controlled, and/or spatial bioactive agent delivery to cells and/or tissue, such as encapsulated cells, for therapeutic applications and tissue engineering applications. The ability to readily form cytocompatible coacervates under mild conditions that permit the compartmentalized encapsulation of cells and/or bioactive agents via simple mixing can be valuable for tissue engineering strategies as it allows for control over their spatial distribution.

In some embodiments, the complex coacervate system described herein can include an oxidized alginate or oxidized methacrylated alginate that when mixed with a methacrylated gelatin forms a plurality of coacervate micro and/or nanodroplets under physiological pH and temperature. The oxidized alginate can be formed by periodate oxidation of alginate using, for example, sodium periodate. Periodate oxidation can cleave the carbon-carbon bond of the cis-diol group in the uronate residue of alginate and alter the chain conformation. The alignate can be oxidized using a periodate to provide an alginate oxidation up to about 50%, for example, about 5% to about 50% or about 10% to about 25%. The oxidized alginate can optionally then be methacrylated by reacting the oxidized alginate with a methacrylate reactant, such as 2-aminoethyl methacrylate, to provide an alginate methacrylation up to about 75%, for example, about 5% to about 45% or about 15% to about 45%. In some embodiment, the oxidized methacrylated alginate can have an alginate oxidation percentage of about 10% to about 25% and an alginate methacrylation percentage of about 10% to about 25%.

The methacrylated gelatin can be prepared by reacting gelatin with maleic anhydride. The gelatin methacrylation percentage can be varied up to about 100%, for example, about 5% to about 99%. Advantageously, the gelatin methacrylation percentage can be at least about 10% (e.g., at about 75%) to enhance formation of the coacervate upon mixing of the oxidized methacrylated alginate and the methacrylated gelatin.

Upon mixing, the methacrylated gelatin can form imine bond-based covalent complexes with the oxidized alginate or oxidized methacrylated alginate and a plurality of coacervate micro and/or nanodroplets that are suspended in a coacervate liquid phase or matrix. The coacervate micro and/or nanodroplets can be substantially and/or uniformly spherical and be distributed substantially uniformly throughout coacervate.

The coacervate micro and/or nanodroplets can be primarily or substantially composed of the methacrylated gelatin with the oxidized alginate or oxidized methacrylated alginate being provided on the microdroplet surface shell and in the surrounding equilibrium phase or matrix of the coacervate. Since methacrylate groups are hydrophobic, methacrylation of alginate and gelatin can increase the hydrophobicity. Because gelatin tends to aggregate by hydrophobic interactions, which is further enhanced by its methacrylation, the methacrylated gelatin can more rapidly aggregate and form coacervate microdroplets within a few seconds.

In some embodiment, the liquid phase surrounding the coacervate micro and/or nanodroplets can be cross-linked so a hydrogel is formed with a plurality of the coacervate micro and/or nanodroplets suspended in a matrix of the hydrogel. Such crosslinks may be between the same or different constituents of the coacervate, and may involve bioactive agents or other materials incorporated therein. There are a number of agents and methods of using the foregoing that may be used to affect such crosslinking. In one embodiment, crosslinking may be affected by use of including a constituent in the coacervate that is photocrosslinkable. For example, the oxidized alginate or oxidized methacrylated alginate can be photocrosslinkable with UV light in the presence of photoinitiators to form a photocrosslinked hydrogel. The photoinitiator can include any photoinitiator that can initiate or induce polymerization or crosslinking of a constituent, such as the oxidized methacrylated alginate, of the coacervate. Examples of photoinitiators can include 2-hydroxy, -4'-(2-hydroxyethoxy)-2-methylpropiophenone, camphorquinone, benzoin methyl ether, 2-hydroxy-2-methyl-1-phenyl-1-propanone, diphenyl (2,4,6-trimethylbenzoyl)phosphine oxide, benzoin ethyl ether, benzophenone, 9,10-anthraquinone, ethyl-4-N, N-dimethylaminobenzoate, diphenyliodonium chloride and derivatives thereof. Other examples are presented in U.S. Pat. No. 5,858,746, which is herein incorporated by reference in its entirety. In addition, any photocrosslinkable constituent of a coacervate may be used as a primer or coupling agent to modify the exterior of the coacervate. For example, such primer or coupling agent may be used to react to enhance biocompatibility and to increase adhesion to cells, cell aggregates, tissues and synthetic materials.

The at least on bioactive agent can be incorporated and/or encapsulated in the coacervate micro and/or nanodroplets to provide localized, sustained, and/or controlled release of the at least one bioactive agents to cells in or about the coacervate micro and/or nanodroplets and/or hydrogels under physiological conditions in a spatial and/or temporally controlled or predetermined manner. By incorporating and/or encapsulating bioactive agent in a coacervate microdroplet, it is possible, in certain embodiments, to provide a steady dosage of such bioactive agent through a sustained or controlled release process. In addition, such encapsulation may protect the bioactive agent, or other materials from undesirable immunogenic, proteolytic or other events that would reduce the efficacy of the bioactive agent. It will be appreciate that the at least one bioactive agent can alternatively or additionally be provided in the hydrogel matrix surrounding the micro and/or nanodroplets to further modify the release of the bioactive agent to cells in or about the micro and/or nanodroplets and/or hydrogel.

The at least one bioactive agent can include polynucleotides and/or polypeptides encoding or comprising, for example, transcription factors, differentiation factors, growth factors, and combinations thereof. The at least one bioactive agent can also include any agent capable of promoting tissue formation (e.g., bone and/or cartilage), destruction, and/or targeting a specific disease state (e.g., cancer). Examples of bioactive agents include chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-$\beta$ I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, DNA encoding for an shRNA of interest, oligonucleotides, proteoglycans, glycoproteins, and glycosaminoglycans.

The bioactive agents can be loaded, incorporated, and/or encapsulated into coacervate micro and/or nanodroplets and/or hydrogel during their preparation. For example, the bioactive agent can be initially combined with the methacrylated gelatin prior to mixing with the oxidized methacrylated alginate so that the bioactive agent is provided in the coacervate micro and/or nanodroplets. Alternatively or additionally, the at least on bioactive agent can be combined with the oxidized methacrylated alginate prior to mixing with the methacrylated gelatin so that the bioactive agent is provided in the surrounding matrix of the hydrogel. The amount of bioactive agent provided in the coacervate micro and/or nanodroplets and/or hydrogel will depend on a number of factors, including: (i) the identity of the bioactive agent; (ii) the coacervate's intended use, including any desired therapeutic effect for in vivo use; (iii) the chemical and physical properties of the coacervate, including the release rate of encapsulated bioactive agent or other material under different conditions.

In certain embodiments, a sufficient amount of the bioactive agent can be incorporated into the coacervate micro and/or nanodroplets and/or hydrogel to produce a therapeutically beneficial result. In those embodiments in which the bioactive agent is a polypeptide, such as BMP-2, the polypeptide loaded in any coacervate may range from less than about 0.05 to more than about 50 weight percent, or about 0.1, 0.25, 0.5, 0.75, 1.0, 1.5, 2.0, 3.0, 4.0, 5.0, 6.0, 7.0, 8.0, 9.0, 10, 15, 20, 25, 30, 35, 40, or 45 weight percent.

In addition to bioactive agents, other materials may be incorporated into a coacervate micro and/or nanodroplets and/or hydrogels. Such additional materials may affect the therapeutic and other characteristics of the coacervate that results. One example of such another material is an adjuvant. (Such materials may also be termed bioactive agents if appropriate.)

Alternatively, materials that augment the therapeutic effect of the bioactive agent may be incorporated into the coacervate micro and/or nanodroplets and/or hydrogel. For example, natural polymers, such as heparin, that control and/or delay the release of the bioactive agent can be provided in the coacervate. (Such materials may also be referred to as bioactive agents as appropriate). The amount of any such augmenting agent to be loaded into any coacervate will depend on a variety of factors, including the nature of the such agent, the coacervate, whether there are any other materials incorporated in addition to the bioactive agent, and the like. For any such agent, the present invention contemplates incorporating a sufficient amount to augment the therapeutic effect of the bioactive agent. In other embodiments, the amount of such augmenting agent may range from about 0.005% up to about 25%, or alternatively 0.01, 0.05, 0.1, 0.25, 0.5, 1.0, 2.5, 5.0, 10, 15 or 20%.

In some embodiments, more than two different bioactive agents can be loaded into the coacervate micro and/or nanodroplets and/or hydrogel. In certain embodiments, three, four, five or more bioactive agents augmenting agents, fillers or other materials may be incorporated in any coacervate microdroplet and/or hydrogel.

The release rate of the bioactive agent in the coacervate micro and/or nanodroplets and/or hydrogel will vary with different embodiments. For example, one subject formulation may require at least an hour to release a major portion of the bioactive agent into the surrounding medium, whereas another formulation may require about 1-24 hours, or even much longer. In certain embodiments, such release may result in release (over, say 1 to about 2,000 hours, or alternatively about 2 to about 800 hours) of the bioactive agent or other material encapsulated in the coacervate micro and/or nanodroplets. In certain embodiments, such substance or other material may be released in an amount sufficient to produce a therapeutically beneficial response.

The release profile of any bioactive agent or other material from the coacervate micro and/or nanodroplets and/or hydrogel may vary in different embodiments. In one embodiment, the bioactive agent or other material is released from the coacervate micro and/or nanodroplets and/or hydrogel in a pulsatile manner. For example, such a pulsatile manner may involve release of the bioactive agent or other material in three phases: an initial burst, a slow release, and a second burst. In another embodiment of the present invention, the bioactive agent or other material is released in a sustained manner. In still other embodiments, a significant portion of the bioactive agent or other material is released in an initial phase. In still other embodiments, the release profile is bi-phasic or multi-phasic.

In other embodiment, the coacervate hydrogel can be biodegradable and/or cytocompatible and include at least one cell dispersed on or within the hydrogel. The plurality of coacervate micro and/or nanodroplets in the hydrogel can provide controlled release of the bioactive agent to the at least one cell provided in the hydrogel. For example, a plurality of cells can be entirely or partly encapsulated within the coacervate hydrogel and the bioactive agent can be controllably release in a spatial or temporal manner to facilitate proliferation, growth, and/or differentiation of the cells. Cells can include any progenitor cell, such as a totipotent stem cell, a pluripotent stem cell, or a multipotent stem cell, as well as any of their lineage descendant cells, including more differentiated cells (described above), such as MSCs.

The cells can be autologous, xenogeneic, allogeneic, and/or syngeneic. Where the cells are not autologous, it may be desirable to administer immunosuppressive agents in order to minimize immunorejection. The cells employed may be primary cells, expanded cells, or cell lines, and may be dividing or non-dividing cells. Cells may be expanded ex vivo prior to introduction into or onto the hydrogel. For example, autologous cells can be expanded in this manner if a sufficient number of viable cells cannot be harvested from the host subject. Alternatively or additionally, the cells may be pieces of tissue, including tissue that has some internal structure. The cells may be primary tissue explants and preparations thereof, cell lines (including transformed cells), or host cells.

Generally, cells can be introduced into the coacervate hydrogel in vitro, although in vivo seeding approaches can optionally or additionally be employed. In some embodiments, the cells may be mixed with the photocrosslinkable oxidized methacrylated alginate prior to mixing with methacrylated gelatin/bioactive agent solution and forming the coacervate. After mixing the cells with the photocrosslinkable oxidized methacrylated alginate, the cell/oxidized methacrylated alginate solution can be mixed with the methacrylated gelatin/bioactive agent solution so that a coacervate is formed with the cells being provided in alginate solution surrounding the coacervate micro and/or nanodroplets. The coacervate can then be crosslinked to form a biodegradable hydrogel with the cells being provided in the hydrogel matrix and at least one bioactive agent being encapsulated in coacervate micro and/or nanodroplets.

If the biodegradable coacervate hydrogel is to be implanted for use in vivo after in vitro seeding, for example, sufficient growth medium may be supplied to ensure cell viability during in vitro culture prior to in vivo application. Once the coacervate hydrogel has been implanted, the nutritional requirements of the cells can be met by the circulating fluids of the host subject.

In other embodiments, cells may be injected into the coacervate hydrogel (e.g., in combination with growth medium) or may be introduced by other means, such as pressure, vacuum, osmosis, or manual mixing. Alternatively or additionally, cells may be layered on the coacervate hydrogel, or the coacervate hydrogel may be dipped into a cell suspension and allowed to remain there under conditions and for a time sufficient for the cells to incorporate within or attach to the coacervate hydrogel. Generally, it is desirable to avoid excessive manual manipulation of the cells in order to minimize cell death during the impregnation procedure. For example, in some situations it may not be desirable to manually mix or knead the cells with the biodegradable coacervate hydrogel; however, such an approach may be useful in those cases in which a sufficient number of cells will survive the procedure. Cells can also be introduced into the coacervate hydrogel in vivo simply by placing the hydrogel in the subject adjacent a source of desired cells. Bioactive agents released from the biodegradable hydrogel may also recruit local cells, cells in the circulation, or cells at a distance from the implantation or injection site.

As those of ordinary skill in the art will appreciate, the number of cells to be introduced into the biodegradable coacervate hydrogel will vary based on the intended application of the hydrogel and on the type of cell used. Where dividing autologous cells are being introduced by injection or mixing into the biodegradable coacervate hydrogel, for example, a lower number of cells can be used. Alternatively, where non-dividing cells are being introduced by injection or mixing into the biodegradable coacervate hydrogel, a larger number of cells may be required.

In another embodiment, coacervate micro and/or nanodroplets and/or hydrogels may contain particles useful to locate the coacervate for diagnostic applications and the like. In certain embodiments, coacervate micro and/or nanodroplets and/or hydrogels may contain paramagnetic, superparamagnetic or ferromagnetic substances which are of use in magnetic resonance imaging (MRI) diagnostics. For example, submicron particles of iron or a magnetic iron oxide may be incorporated into coacervate micro and/or nanodroplets and/or hydrogels to provide ferromagnetic or superparamagnetic particles. Paramagnetic MRI contrast agents principally comprise paramagnetic metal ions, such as gadolinium ions, held by a chelating agent which prevents their release (and thus substantially reduces their toxicity). In another embodiment, coacervate micro and/or nanodroplets and/or hydrogels may contain submicron particles, such as magnetic iron oxide, which permit the magnetic separation of coacervates. Other labeled compounds, such as radionucleides, e.g., $^3H$, $^{14}C$, $^{18}F$, $^{32}P$, $^{99m}Tc$, and $^{125}I$, may also be utilized for visualizing cells and tissues, to which coacervate micro and/or nanodroplets and/or hydrogels may be bound, by means of X-rays or magnetic resonance imaging. Coacervate micro and/or nanodroplets and/or hydrogels may also contain in certain embodiments, ultrasound contrast agents, such as heavy materials, e.g., barium sulphate or iodinated compounds, to provide ultrasound contrast media.

In still other embodiments, the coacervate micro and/or nanodroplets and/or hydrogels may be conjugated to targeting molecules attached to the surface of the coacervate microdroplet and/or hydrogel, such as monoclonal antibodies that preferentially bind to a receptor or other site of interest. In certain embodiments, such targeting may achieve targeted delivery in vivo of the micro and/or nanodroplets and/or hydrogel. To attach targeting molecules to the surface of any coacervate micro and/or nanodroplets and/or hydrogels, it may be necessary to provide coacervates linker molecules. Such linker molecules may be used to attach targeting molecules. Alternatively, the constituents that form the coacervate micro and/or nanodroplets and/or hydrogels may contain functional groups that allow for attachment of targeting molecules.

The coacervate micro and/or nanodroplets and/or hydrogels can be injectable and/or implantable, and can be in the form of a membrane, sponge, gel, solid scaffold, spun fiber, woven or unwoven mesh, nanoparticle, microparticle, or any other desirable configuration. The coacervate micro and/or nanodroplets and/or hydrogels can be used in a variety of biomedical applications, including tissue engineering, drug discovery applications, and regenerative medicine and cancer therapy.

In one example, a biodegradable coacervate hydrogel comprising suspended chondrogenic cells, such as MSCs, and growth factor (e.g., BMP-2) encapsulated coacervate micro and/or nanodroplets can be used in a method to promote tissue growth in a subject. One step of the method can include identifying a target site. The target site can comprise a tissue defect (e.g., cartilage and/or bone defect) in which promotion of new tissue (e.g., cartilage and/or bone) is desired. The target site can also comprise a diseased location (e.g., tumor). Methods for identifying tissue defects and disease locations are known in the art and can include, for example, various imaging modalities, such as CT, MRI, and X-ray.

The tissue defect can include a defect caused by the destruction of bone or cartilage. For example, one type of cartilage defect can include a joint surface defect. Joint surface defects can be the result of a physical injury to one or more joints or, alternatively, a result of genetic or environmental factors. Most frequently, but not exclusively, such a defect will occur in the knee and will be caused by trauma, ligamentous instability, malalignment of the extremity, meniscectomy, failed ACI or mosaicplasty procedures, primary osteochondritis dessecans, osteoarthritis (early osteoarthritis or unicompartimental osteochondral defects), or tissue removal (e.g., due to cancer). Examples of bone defects can include any structural and/or functional skeletal abnormalities. Non-limiting examples of bone defects can include those associated with vertebral body or disc injury/destruction, spinal fusion, injured meniscus, avascular necrosis, cranio-facial repair/reconstruction (including dental repair/reconstruction), osteoarthritis, osteosclerosis, osteoporosis, implant fixation, trauma, and other inheritable or acquired bone disorders and diseases.

Tissue defects can also include cartilage defects. Where a tissue defect comprises a cartilage defect, the cartilage defect may also be referred to as an osteochondral defect when there is damage to articular cartilage and underlying (subchondral) bone. Usually, osteochondral defects appear on specific weight-bearing spots at the ends of the thighbone, shinbone, and the back of the kneecap. Cartilage defects in the context of the present invention should also be understood to comprise those conditions where surgical repair of cartilage is required, such as cosmetic surgery (e.g., nose, ear). Thus, cartilage defects can occur anywhere in the body where cartilage formation is disrupted, where cartilage is damaged or non-existent due to a genetic defect, where cartilage is important for the structure or functioning of an organ (e.g., structures such as menisci, the ear, the nose, the larynx, the trachea, the bronchi, structures of the heart valves, part of the costae, synchondroses, enthuses, etc.), and/or where cartilage is removed due to cancer, for example.

After identifying a target site, such as a cranio-facial cartilage defect of the nose, the biodegradable hydrogel can be administered to the target site. The coacervate hydrogel can be prepared according to the method described above.

Next, the biodegradable hydrogel may be loaded into a syringe or other similar device and injected or implanted into the tissue defect. Upon injection or implantation into the tissue defect, the biodegradable coacervate hydrogel can be formed into the shape of the tissue defect using tactile means.

After implanting the biodegradable hydrogel into the subject, the progenitor cells can begin to migrate from the hydrogel into the tissue defect, express growth and/or differentiation factors, and/or promote chondroprogenitor cell expansion and differentiation. Additionally, the presence of the biodegradable coacervate hydrogel in the tissue defect may promote migration of endogenous cells surrounding the tissue defect into the biodegradable hydrogel.

The following example is for the purpose of illustration only and is not intended to limit the scope of the claims, which are appended hereto.

EXAMPLE 1

In this Example, we describe we describe the spontaneous formation and properties of coacervates and/or coacervate-laden photocrosslinked hydrogels (i.e., coacervate hydrogels) derived from the simple mixing of OMA and GelMA in aqueous solution at a wide pH range and room temperature, and demonstrate that the resultant compartments can be utilized as novel platforms for localized, sustained bioactive molecule delivery systems with the capacity for the simultaneous encapsulation of stem cells, such as mesenchymal stem cells (MSCs), for therapeutic applications like bone tissue engineering.

Methods

Preparation of OMA/GelMA Coacervates

All macromers were dissolved separately in Dulbecco's phosphate buffered saline (PBS, 20 w/v %) with a photoinitiator (2-Hydroxy-4'-(2-hydroxyethoxy)-2-methylpropiophenone, 0.05 w/v %, Sigma). GelMA solutions were added to the OMA solutions at an equal volume ratio, followed by mixing for 1 min, to produce the OMA/GelMA coacervate microdroplets. The OMA/GelMA coacervate microdroplet solutions were spread on cover slips, and imaged using a fluorescence microscope (ECLIPSE TE 300, Nikon) equipped with a digital camera (Retiga-SRV, QImaging). Complete detailed methodology can be found in Supplementary Information.

Preparation and Characterization of Oxidized and Methacrylated Alginate (OMA)

The oxidized alginate (OA) was prepared by reacting sodium alginate (Protanal LF 20/40, 196,000 g/mol, FMC Biopolymer) with sodium periodate (Sigma) using a modification of a previously described method. Briefly, sodium alginate (10 g) was dissolved in ultrapure deionized water (diH$_2$O, 900 ml) overnight. Sodium periodate (1.00, 1.75 and 2.50 g) was dissolved in 100 ml diH$_2$O and added to separate alginate solutions to achieve different degrees of theoretical alginate oxidation (10, 17.5 and 25%, respectively) under stirring in the dark at room temperature (RT) for 24 hrs. The oxidized, methacrylated alginate (OMA) macromer was prepared by reacting OA with 2-aminoethyl methacrylate (AEMA, Sigma). To synthesize OMA, 2-morpholinoethanesulfonic acid (MES, 19.52 g, Sigma) and NaCl (17.53 g) were directly added to an OA solution (1 L) and the pH was adjusted to 6.5. N-hydroxysuccinimide (NHS, 0.88, 1.47 and 2.65 g; Sigma) and 1-ethyl-3-(3-dimethylaminopropyl)-carbodiimide hydrochloride (EDC, 2.92, 4.86, and 8.75 g; Sigma) (molar ratio of NHS:EDC=1:2) were added to the mixture to activate 15, 25 and 45% of the carboxylic acid groups of the alginate, respectively. After 5 min, AEMA (1.27, 2.11 and 3.80 g) (molar ratio of NHS:EDC:AEMA=1:2:1) was added to the product, respectively, and the reaction was maintained in the dark at RT for 24 hrs. The reaction mixture was precipitated with the addition of excess of acetone, dried in a fume hood overnight, and rehydrated to a 1% w/v solution in diH$_2$O for further purification. The OMA was purified by dialysis against diH$_2$O (MWCO 3500; Spectrum Laboratories Inc.) for 3 days, treated with activated charcoal (0.5 mg/100 ml, 50-200 mesh, Fisher, Pittsburgh, Pa.) for 30 min, filtered (0.22 µm filter) and lyophilized To determine the levels of alginate oxidation and methacrylation, the OMAs were dissolved in deuterium oxide (D$_2$O, 2 w/v %), and $^1$H-NMR spectra were recorded on a Varian Unity-300 (300 MHz) NMR spectrometer (Varian Inc.) using 3-(trimethylsilyl) propionic acid-d$_4$ sodium salt (0.05 w/v %) as an internal standard. The actual oxidation and methacrylation (Table 1) of OMAs were calculated from $^1$H-NMR spectra (FIG. 1) based on a previously described method.

TABLE 1

Actual oxidation (%) and methacrylation (%) of OMAs, and actual methacrylation (%) of GelMA

| Code | Theoretical oxidation (%)[a] | Theoretical methacrylation (%)[b] | Actual oxidation (%)[c] | Actual methacrylation (%) |
|---|---|---|---|---|
| 10OX15MA | 10 | 15 | 9.05 | 7.54[d] |
| 10OX25MA | 10 | 25 | 9.05 | 11.89[d] |
| 10OX45MA | 10 | 45 | 9.05 | 16.93[d] |
| 17.5OX15MA | 17.5 | 15 | 14.22 | 10.23[d] |
| 17.5OX25MA | 17.5 | 25 | 14.22 | 14.09[d] |
| 17.5OX45MA | 17.5 | 45 | 14.22 | 19.23[d] |
| 25OX15MA | 25 | 15 | 20.17 | 10.74[d] |
| 25OX25MA | 25 | 25 | 20.17 | 16.39[d] |
| 25OX45MA | 25 | 45 | 20.17 | 21.38[d] |
| L-GelMA-A | — | — | — | 6.54[e] |
| L-GelMA-B | — | — | — | 7.83[e] |
| H-GelMA-A | — | — | — | 97.39[e] |
| H-GelMA-B | — | — | — | 93.23[e] |

[a]Theoretical oxidation of uronic acid units of alginate was calculated based on the mass of alginate in 1 w/v % solution and the molecular weight of the repeat unit (M$_0$ = 198).
[b]Theoretical methacrylation of the alginate carboxylic acid reactive groups was calculated based on the mass of alginate in 1 w/v % solution and the molecular weight of the repeat unit (M$_0$ = 198).
[c]Actual alginate oxidation was calculated from $^1$H-NMR data based on a previously described method.
[d]Actual methacrylation of OMA was calculated from $^1$H-NMR data based on a previously described method.
[e]Actual methacrylation of GelMA was calculated from $^1$H-NMR data based on a previously described method.

The highly methacrylated type-A gelatin (H-GelMA-A) and type-B gelatin (H-GelMA-B) were synthesized by reaction of type-A gelatin and type-B gelatin with methacrylic anhydride using a modification of a previously described method. Briefly, porcine skin type-A gelatin (10 g, Sigma) and bovine type-B gelatin (10 g, Sigma) were separately dissolved in 100 mL Dulbecco's phosphate buffered saline (PBS, Gibco) at 60° C. and stirred until fully dissolved. Methacrylic anhydride (10 mL, Sigma, purity ≥92%) was added at a rate of 0.5 mL/min to each gelatin solution under stirring at 50° C., and the reaction was maintained in the dark at RT for 3 hrs. Less methacrylic anhydride (0.5 mL) was used to prepare GelMA with a lower degree of methacrylation (L-GelMA). The reaction mixture was precipitated into excess acetone, dried in fume hood and rehydrated to a 10 w/v % solution in diH$_2$O. The GelMAs were purified by dialysis against diH$_2$O (MWCO 12-14 kDa) for 7 days at 40° C. to remove salts, unreacted methacrylic anhydride and byproducts, filtered (0.22 µm filter) and lyophilized To analyze the degree of methacrylation of GelMAs, $^1$H-NMR spectra of GelMA in D$_2$O were recorded as described above. The actual methacrylation of GelMAs (Table 1) were calculated from the $^1$H-NMR spectra (FIG. 2) based on a previously described method.

Fluorescent Labeling of OMA and GelMA

Images of OMA/GelMA coacervates formed with fluorescently labeled components can demonstrate the structure of the coacervate microdroplets. Therefore, the OMA and GelMA were labeled with different fluorescent dyes to reveal this structure. OMA (1 g, 17.5OX15MA) was dissolved in 100 ml MES buffer (50 mM MES, 0.5 M NaCl, and pH 6.5). NHS (0.58 g) and EDC (1.94 g) (molar ratio of NHS:EDC=1:2) were added to the OMA solution to activate the carboxylic acid groups of the OMA. After 5 min, a blue fluorescent dye (1 mg, CF™ 350 hydrazide, Biotium) was added to the OMA solution, and the reaction was maintained in the dark at RT for 24 hrs. H-GelMA-A (1 g) was dissolved in 100 ml MES buffer (50 mM MES, 0.5 M NaCl, and pH 6.5), a red fluorescent dye (0.82 mg, CFTM633 succinimidyl ester, Biotium) was added to the GelMA solution, and the reaction was maintained in the dark at RT for 24 hrs. The macromers were precipitated in excess acetone, dried in a fume hood overnight, and rehydrated to a 1% w/v solution in $diH_2O$ for further purification. The fluorescently labeled OMA and GelMA were purified by dialysis against $diH_2O$ (MWCO 12~14 k Da; Spectrum Laboratories Inc.) for 3 days, filtered (0.22 µm filter) and lyophilized. The OMA/GelMA coacervate microdroplets were prepared, spread on a cover slip, and imaged using a fluorescence microscope (ECLIPSE TE 300, Nikon) equipped with a digital camera (Retiga-SRV, QImaging).

Preparation of OMA/GelMA Coacervates

All OMAs and GelMAs (20 w/v %) were dissolved separately in PBS with a photoinitiator (2-Hydroxy-4'-(2-hydroxyethoxy)-2-methylpropiophenone, 0.05 w/v %, Sigma) at pH 7.4. GelMA solutions were added to the OMA solutions at an equal volume ratio, followed by mixing for 1 min by pipetting, to produce the OMA/GelMA coacervate microdroplets. The OMA/GelMA coacervate microdroplet solutions were spread on cover slips, and were imaged using a microscope (ECLIPSE TE 300) equipped with a digital camera (Retiga-SRV). The coacervate microdroplet diameters were measured using NIH ImageJ analysis software (n>400 per group). The average size of the coacervate microdroplets was significantly smaller for GelMA-A compared to GelMA-B (FIG. 3D-U). As the theoretical degree of alginate oxidation significantly increased from 10 to 17.5%, the size of coacervate microdroplets increased. The size of coacervate microdroplets also significantly increased as the theoretical degree of alginate methacrylation increased from 15 to 25% (FIG. 3D-U).

To fabricate OMA/GelMA coacervate microdroplet-laden photocrosslinked hydrogels, 10OX45MA, 17.5OX45MA and 25OX45MA OMA solutions were each mixed with an equal volume of H-GelMA-B solution for 1 min by pipetting, placed between quartz (top) and glass (bottom) plates separated by 0.4 mm spacers, photocrosslinked with 365 nm UV light (Omnicure® S1000, EXFO Photonic Solution Inc.) at ~3.0 $mW/cm^2$ for 5 min, and then imaged using a microscope (ECLIPSE TE 300) equipped with a digital camera (Retiga-SRV).

The elastic moduli of OMA/GelMA coacervate microdroplet-laden photocrosslinked hydrogels were determined by performing uniaxial, unconfined constant strain rate compression tests at room temperature using a constant crosshead speed of 1%/sec on a mechanical testing machine (225 lbs Actuator, TestResources) equipped with a 5 N load cell. Elastic moduli were calculated from the first non-zero linear slope of the stress versus strain plots over 5% strain (N=3). The compressive moduli of coacervate microdroplet-laden photocrosslinked hydrogels formed with H-GelMA-A (Figure S3v) were significantly higher than H-GelMA-B (FIG. 3W) when formed with the same OMA, except for the 10OX25MA and 10OX45MA compositions. The compressive moduli significantly increased as the degree of alginate methacrylation increased. In contrast, as the degree of alginate oxidation increased, the compressive moduli significantly decreased (FIG. 3V-W).

Turbidity Measurements of OA/Gelatin, OA/GelMA, OMA/Gelatin and OMA/GelMA Mixtures All macromers were dissolved separately in PBS (20 w/v %) with a photoinitiator (0.05 w/v %) at pH 7.4. To measure the turbidity of alginate and gelatin mixtures, 100 µL of OA or OMA solutions were placed in wells of a 96-well plate and then mixed with 100 µL of gelatin or GelMA solutions using a pipette for 1 min. The absorbance (turbidity) at 500 nm was measured before and after mixing using a microplate reader (VersaMax, Molecular Devices). The turbidity of OAs/gelatins (FIG. 4A), OMAs/gelatins (FIG. 4B), and OAs/L-GelMAs (FIG. 4C) did not significantly increase after mixing, indicating no coacervate formation, while OAs/H-GelMAs exhibited significant increases in turbidity (FIG. 4D). Interestingly, the turbidity of OMAs/L-GelMAs exhibited greater increases after mixing as OMA methacrylation increased (FIG. 4E), indicating the extent of OMA/GelMA coacervate formation is also affected by the degree of alginate methacrylation.

To evaluate the effect of the degree of gelatin methacrylation on coacervate formation, 100 µL of OA (25% theoretical oxidation) solution was mixed with 100 µL of gelatin solution containing various weight fractions of H-GelMA-A in 96-well plate using a pipette for 1 min, and then the turbidity at 500 nm was measured using a microplate reader (VersaMax).

Osteogenesis of Photoencapulated hMSCs by BMP-2 Delivery from OMA/GelMA Coacervate Hydrogel To evaluate the release kinetics of BMP-2 from photocrosslinked OMA/GelMA coacervate hydrogels, OMA (20 w/v %, 25OX45MA) and H-GelMA-A (20 w/v %) were dissolved separately in PBS containing 0.05 w/v % photoinitiator (Sigma). BMP-2 (8 µg, R&D systems, 1 µg/µL) and $I^{125}$-labeled BMP-2 (16 µL, 250 µCi/mL, Perkin Elmer) were added to the OMA or GelMA solution. After gently mixing for 5 min, a 50 µL aliquot of OMA solution was placed a well of a 96-well plate and then mixed with an equal volume of GelMA solution using a pipette for 1 min. The mixtures were photocrosslinked with 365 nm UV light (Omnicure) at ~3.0 $mW/cm^2$ for 5 min to form the hydrogels. The final concentrations of photoencapsulated growth factors were 1 µg BMP-2 and 0.5 µCi $I^{125}$-labeled BMP-2 per 100 µL hydrogel. Each photocrosslinked hydrogel was then placed in a 15-ml conical tube containing 5 mL PBS (pH 7.4) and incubated at 37° C. At predetermined time points over the course of eight weeks, the supernatant was withdrawn and fresh PBS was replenished. Aliquots (50 µl) of supernatant were emulsified with Optiphase HighSafe-2 scintillation cocktail solution (150 µl, Perkin-Elmer) in 96-well microplates for 1 min. The radioactivity in the supernatants was determined using a Wallac 1450 Microbeta liquid scintillation counter (Perkin-Elmer). The cumulative BMP-2 release from the photocrosslinked OMA/GelMA coacervate hydrogels at each time point was normalized as a percentage of total BMP-2 incorporated. To functionalize OMA/GelMA coacervate hydrogels with heparin, methacrylated heparin (heparin:OMA or GelMA=1:9 weight ratio) was added to OMA or GelMA solutions prior to addition of BMP-2 (8 µg) and $I^{125}$-labeled BMP-2 (16 µL). After coacervate formation and subsequent photocrosslinking, the release study was performed in PBS as described above.

To isolate hMSCs, bone marrow aspirates were obtained from the posterior iliac crest of healthy donors under a protocol approved by the University Hospitals of Cleveland Institutional Review Board and processed as previously described. Briefly, the aspirates were washed with growth medium comprised of low-glucose Dulbecco's Modified Eagle's Medium (DMEM-LG, Sigma) with 10% pre-screened fetal bovine serum (FBS, Gibco). Mononuclear cells were isolated by centrifugation in a Percoll (Sigma) density gradient and the isolated cells were plated at $1.8\times10^5$ cells/cm² in DMEM-LG containing 10% FBS and 1% penicillin/streptomycin (P/S, Thermo Fisher Scientific) in an incubator at 37° C. and 5% $CO_2$. After 4 days of incubation, non-adherent cells were removed and adherent cell were maintained in DMEM-LG containing 10% FBS and 1% P/S with media changes every 3 days. After 14 days of culture, the cells were passaged at a density of $5\times10^3$ cells/cm².

To evaluate the osteogenic efficacy of BMP-2 delivery using photocrosslinked OMA/GelMA coacervate microdroplet-embedded hydrogels, OMA (20 w/v %, 25OX45MA) and H-GelMA-A (20 w/v %) were dissolved separately in DMEM-LG containing 0.05 w/v % photoinitiator. BMP-2 (5 µg/100 µl macromer solution) was added to the OMA or GelMA solution, and then the hMSCs (passage number 3, $10\times10^6$ cells/ml) were suspended in OMA solution. After mixing the OMA solution with an equal volume of GelMA solution, the cell/coacervate solutions were injected between two glass plates separated by 0.75 mm spacers and photocrosslinked with 365 nm UV light at ~3 mW/cm² for 5 min to form the hydrogel-cell constructs. Photocrosslinked hydrogel-cell construct disks were created using an 8 mm diameter biopsy punch, placed in wells of 24-well tissue culture plates with 1 ml osteogenic media [10 mM β-glycerophosphate (CalBiochem), 50 µM ascorbic acid (Wako), and 100 nM dexamethasone (MP Biomedicals)] containing 10% FBS and 1% P/S, and cultured in a humidified incubator at 37° C. with 5% $CO_2$ for 112 days.

The viability of encapsulated hMSCs in the photocrosslinked OMA/GelMA coacervate hydrogels was investigated using a Live/Dead assay comprised of fluorescein diacetate [FDA, 1.5 mg/ml in dimethyl sulfoxide (Research Organic Inc.), Sigma] and ethidium bromide (EB, 1 mg/ml in PBS, Thermo Fisher Scientific). The staining solution was freshly prepared by mixing 1 ml FDA solution and 0.5 ml EB solution with 0.3 ml PBS (pH 8). At predetermined time points, 20 µl of staining solution was added into each well and incubated for 3-5 min at room temperature, and then stained hydrogel-cell constructs were imaged using a fluorescence microscope (ECLIPSE TE 300) equipped with a digital camera (Retiga-SRV).

To determine whether hMSCs cultured in growth factor-laden photocrosslinked OMA/GelMA coacervate hydrogels undergo osteogenic differentiation in vitro, at predetermined time points each hydrogel-cell construct was removed from the 24-well plates, put in 1 ml ALP lysis buffer and homogenized at 35,000 rpm for 30 s using a TH homogenizer (Omni International). The homogenized solutions were centrifuged at 500 g with a Sorvall Legent RT Plus Centrifuge (Thermo Fisher Scientific). The supernatants were collected for ALP, calcium and DNA analysis (N=3). For ALP measurement, supernatant (100 µl) was treated with p-nitrophenylphosphate ALP substrate (pNPP, 100 µl, Sigma) at 37° C. for 30 min, and then 0.1 N NaOH (50 µl) was added to stop the reaction. The absorbance was measured at 405 nm using a plate reader (VersaMax). Calcium content of the encapsulated hMSCs was also quantified using a calcium assay kit (Pointe Scientific) according to the manufacturer's instructions. Supernatant (4 µl) was mixed with a color and buffer reagent mixture (250 µl) and the absorbance was read at 570 nm on a microplate reader. DNA content in supernatant was also measured using a Picogreen assay kit (Invitrogen) according to the manufacturer's instructions. Fluorescence intensity of the dye-conjugated DNA solution was measured using a fluorescence microplate reader (FMAX, Molecular Devices) set at 485 nm excitation and 538 nm emission. All ALP and calcium content measurements were normalized to DNA content. To visualize the calcium deposition in the hydrogel disks, hydrogel-cell constructs were fixed with 4% paraformaldehyde for 40 min, stained with Alizarin Red S (2 w/v %, pH 4.2; Sigma) for 5 min, and imaged using a digital camera (iPhone 5, Apple). Fixed hydrogel-cell constructs were embedded in paraffin, sectioned at a thickness of 10 µm, stained with Alizarin Red S, and then imaged using a microscope (Lenz Laborlux S, Leica) equipped with a digital camera (Coolpix 995, Nikon).

RNA was isolated from hydrogel-cell constructs (N=6) with TRI Reagent (Sigma), and first-strand cDNA was synthesized with a cDNA synthesis kit (PrimeScript RT Reagent Kit with gDNA Eraser, Dakara Bio) according to the manufacturer's instructions. qRT-PCR was performed with a SYBR Premix Ex Tag II (Tli RNase H Plus) kit (Takara Bio) according to the manufacturer's instructions. The primer sequences used for qRT-PCR are in Table 2. All reactions were run on an ABI 7500 Real-Time PCR instrument (Applied Biosystems) for 30 sec at 95° C. followed by 40 cycles of a two-step thermocycling program: 5 sec denaturing at 95° C., 34 sec annealing/extension at 60° C. Results were analyzed with SDS software (Applied Biosystems) and the RQ (relative quantity) Manager Software (Applied Biosystems) for automated data analysis. Relative expression for the target gene of interest (TGI) was normalized to GAPDH using the delta threshold cycle ($\Delta Ct$) method. Namely, the Ct for each gene and endogenous control GAPDH in each sample were used to create a $\Delta Ct_{TGI}$ value ($Ct_{TGI}$-$Ct_{GAPDH}$). Thereafter, $\Delta\Delta Ct$ values were calculated by subtracting the $\Delta Ct_{TGI}$ of the control (OMA/GelMA) without BMP-2 from the $\Delta Ct_{TGI}$ of experimental groups. The relative expression of target gene was calculated using the equation: $2^{-\Delta\Delta Ct}$.

TABLE 2

Primer sequences used for qRT-PCR

| Gene | Direction | Primer sequences | Accession number |
|---|---|---|---|
| GAPDH | Forward Reverse | GGGGCTGGCATTGCCCTCAAGGCTGGT GGTCCAGGGGTCT (SEQ ID NO: 1) | NM_002046 |
| Runx2 | Forward Reverse | ACAGAACCACAAGTCGGTGCAATGGC TGGTAGTGACCTGCGGA (SEQ ID NO: 2) | NM_004348 |
| BSP | Forward Reverse | ACCCTAACCCTGGAGAGCCCCTTCGCC TTGAGATATCGGGGGCA (SEQ ID NO: 3) | NM_004967 |

Results

OMA was prepared by functionalization of alginate by both oxidation and methacrylation (FIG. 8A), and GelMA was synthesized by methacrylating gelatin (FIG. 8B). By mixing aqueous solutions of OMA and GelMA, imine bond-based complex coacervate microdroplets can form via Schiff base reaction between the aldehyde groups of the OMA and the amine groups of the GelMA (FIG. 8C). In this manner, micron-scale coacervates (FIGS. 8D-F and FIGS. 3A-B) and coacervate-laden hydrogels formed by photocrosslinking immediately after mixing (FIG. 3C) were easily generated. The morphological changes in the OMA/GelMA coacervates resulting from varying the degrees of alginate oxidation and methacrylation were first investigated. When varying the theoretical methacrylation level of OMA (15, 25 and 45%) while keeping a constant theoretical oxidation level of 10% (10OX15MA, 10OX25MA, and 10OX45MA), after mixing with highly methacrylated type-A gelatin (H-GelMA-A) and type-B gelatin (H-GelMA-B) solutions, coacervate microdroplets formed that were not uniformly spherical in structure. In contrast, solutions of H-GelMA mixed with OMAs of 17.5% and 25% theoretical oxidation exhibited relatively homogeneous spherical complex coacervate microdroplets (FIG. 3A-B). Since the crosslinking by imine bond-based complexation between OMA and H-GelMA depends on the number of aldehyde groups of OMA, and 17.5OX and 25OX OMA had 1.57 and 2.23-fold higher aldehyde groups than 10OX OMAs (Table 1), respectively, it is likely that the OMA/H-GelMA coacervate microdroplets have higher crosslinking density with increasing alginate oxidation level, which could enhance the physical stability of coacervate microdroplets.

Since turbidity is one of most important indicators to confirming coacervation, we evaluated turbidity before and after mixing of the two solutions by absorbance measurement at 500 nm to determine the degrees of complex coacervate formation. Regardless of gelatin type and alginate oxidation and methacrylation level, the turbidity of all conditions significantly increased after mixing, indicating complex coacervate formation (FIG. 8G). As the alginate oxidation level increased, the turbidity of the OMA/H-GelMA complex coacervates also exhibited an increasing trend, indicating more stable coacervate formation. This result was well correlated with microscopic examination of the morphology of the coacervates. However, as the alginate methacrylation level increased, which could decrease the number of negatively charged carboxylic acid groups in alginate, the turbidity of the OMA/H-GelMA coacervates showed a decreasing trend. This result indicates that the electrostatic interactions of carboxylic acid groups of OMA and amine groups of H-GelMA could also affect the coacervate formation of OMA and H-GelMA.

The phase separation in typical complex coacervation is primarily caused by the electrostatic interactions between oppositely charged polyelectrolytes such as proteins and polymers. Therefore, pH, which influences the ionic strength of polyelectrolytes, plays a fundamental role in the formation of complexes between oppositely charged polyelectrolytes. Since the capacity for complex coacervate formation by the alginate/gelatin system has exhibited a strong dependence on pH in previous reports, the turbidity of OMA/GelMA coacervates at various pHs (2.07~11.57) was measured to determine if there was a similar pH dependency for these functionalized polymers. Interestingly, the mixtures of OMA and H-GelMA formed coacervates at a wide range of pH, demonstrating a pH independency, with higher turbidity observed at lower pH (FIG. 8H). This result indicates that the complex coacervates were mainly formed through imine bond formation by Schiff base reaction, which takes place at a wide range of pHs, between the aldehyde groups of OMA and the amine groups of H-GelMA as shown in FIG. 8C, while the electrostatic interactions between the carboxylic groups of OMA and the amine groups of H-GelMA had greater affect on the complex coacervate formation at lower pH, which is in agreement with the literature.

Figure 2:
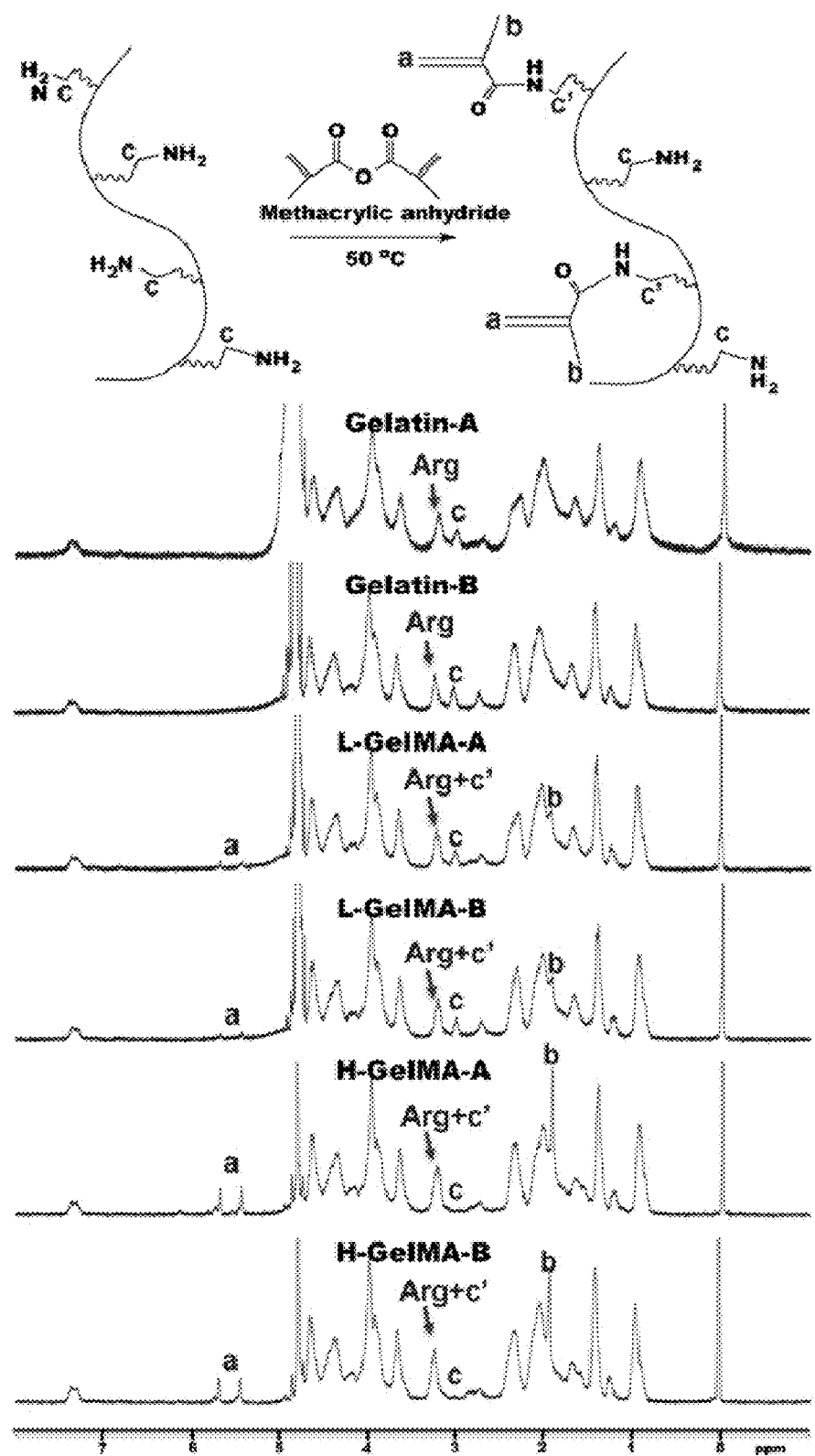
FIG. 2 illustrates $^1$H-NMR spectra of gelatins and GelMAs with various degrees of methacrylation in $D_2O$. The GelMAs were dissolved in $D_2O$ (2 w/v %), and $^1$H-NMR spectra were recorded on a Varian Unity-300 (300 MHz) NMR spectrometer (Varian Inc.) using 3-(trimethylsilyl)propionic acid-$d_4$ sodium salt (0.05 w/v %) as an internal standard.

Since the spatial distribution of polymers can significantly influence the properties of complex coacervate systems, OMA and GelMA were modified with water-soluble blue fluorescent CF™-350 and red fluorescent CF™-633 dyes, respectively (FIGS. 9A and B) to visualize the distribution of the polymers in this coacervate system. As shown in FIGS. 2C-E, coacervate microdroplets were primarily composed of H-GelMA-A (red), while OMA (blue) was mainly observed in the surrounding equilibrium phase. Furthermore, high-magnification images of an individual coacervate microdroplet showed that H-GelMA-A was uniformly distributed throughout the coacervate microdroplet (FIGS. 9F and H), while OMA was observed on the surface shell of coacervate microdroplet (FIGS. 9G and H). FIG. 9I schematically illustrates the proposed mechanism of OMA/GelMA coacervate formation and resulting microstructure. Upon mixing the two solutions (FIG. 9I-L), the GelMA can form imine bond-based covalent complexes with OMA (FIG. 9I-2) regardless of GelMA and OMA's ionic charge. Since methacrylate groups are hydrophobic, methacrylation of alginate and gelatin could increase the hydrophobicity. Because gelatin tends to aggregate by hydrophobic interactions, which is further enhanced by its methacrylation, GelMA can more rapidly aggregate and form coacervate droplets within a few seconds. Finally, OMA/GelMA complexes were located on the surface of coacervate microdroplets and formed an outer boundary (FIGS. 9G and 2I-3), which could stabilize OMA/GelMA coacervate microdroplets after mixing the solutions.

To further support our proposed mechanism for OMA/GelMA coacervation, which is induced by the crosslinking by imine bond formation between OMA and GelMA, and examine a potential key role of the methacrylate groups of GelMA in coacervate formation, we evaluated coacervate formation using oxidized alginate (OA), OMA, Gelatin-A and GelMA-A. The mixtures of OA/Gelatin-A (FIG. 10A), OMA/Gelatin-A (FIG. 10B), and OA/Gelatin-A with low level of methacrylation (L-GelMA-A) (FIG. 10C) did not form coacervates, but instead formed chemically crosslinked and transparent hydrogels. In contrast, mixtures of OA/Gelatin-A with high level of methacrylation (H-GelMA-A) (FIG. 10D), OMA/L-GelMA-A (FIG. 10E), and OMA/H-GelMA-A (FIG. 10F) formed coacervate microdroplets. These results were further confirmed by turbidity measurements of the mixtures (FIG. 4A-E).

Based on these results, we proposed the structure of each system and confirmed it through fluorescence microscopy. In the OA and Gelatin-A mixture without any methacrylate groups, macromers and water molecules were homogenously distributed in the imine bond-crosslinked hydrogels (FIG. 10G). OMA/Gelatin-A (FIG. 10H) and OA/L-GelMA-A (FIG. 10I) mixtures were also crosslinked by imine bond formation, but hydrophobic interactions by crosslinking and methacrylation were insufficient to induce phase separation due to the low concentration of methacrylates. Therefore, they also formed crosslinked transparent hydrogels. This was not the case for OA/H-GelMA-A (FIG. 10J), OMA/L-GelMA-A (FIG. 10K) and OMA/H-GelMA-A (FIG. 10L) mixtures, however, which had sufficient number of hydrophobic domains that consisted of chemical crosslinking and methacrylate groups, and in turn induced liquid-liquid phase separation to form coacervates. The fluorescence photomicrographs provide microstructural data that supports the proposed mechanism for coacervate formation in this system.

Since solutions of OA with L-GelMA-A did not form a complex coacervate but H-GelMA-A did, this indicates that methacrylate concentration in the gelatin solution plays an important role in the process. To elucidate the relationship between coacervate formation and gelatin methacrylation level, turbidity measurements were taken of mixtures of OA solution with gelatin solutions containing various weight fractions of H-GelMA-A. The turbidity of the mixture gradually increased as the H-GelMA-A content increased up to 10% in gelatin solution, and then rapidly increased at >10% H-GelMA-A in the gelatin solution (FIG. 4F). This result clearly demonstrates the dependence of OMA/GelMA coacervate formation on the concentration of hydrophobic methacrylate groups in the gelatin solution.

Figure 5:
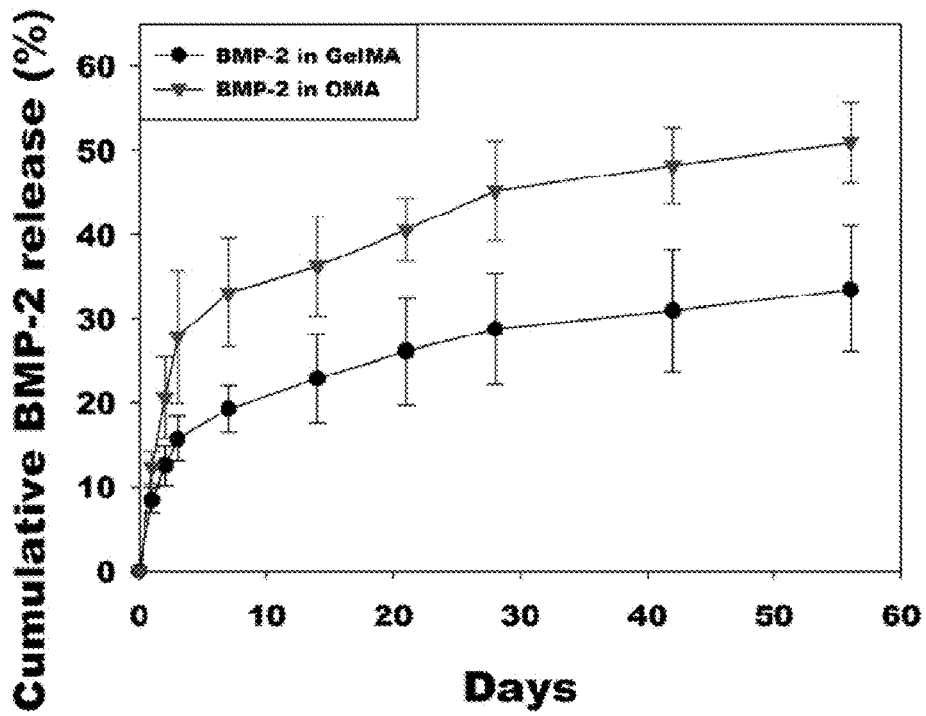
FIG. 5 illustrates a plot showing release profiles of BMP-2 from photocrosslinked heparin-modified OMA/BMP-2 in GelMA (black circle) and BMP-2 in OMA/GelMA (red triangle) coacervate hydrogels (N=5).
Figure 6A:
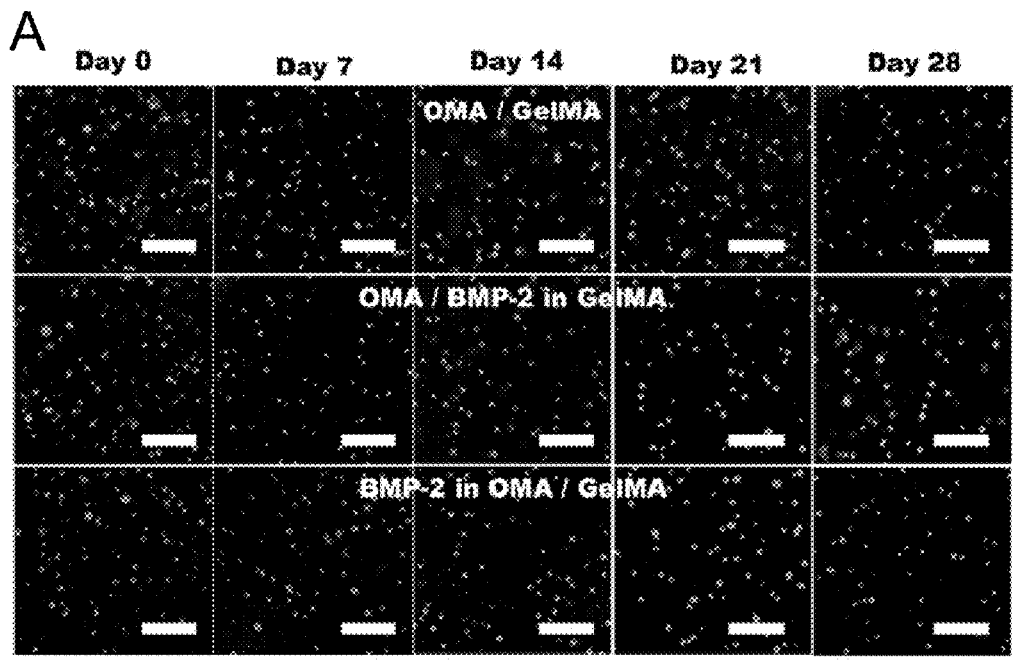
FIGS. 6(A-B) illustrate (A) Representative live/dead images of encapsulated hMSCs in photocrosslinked OMA/GelMA, OMA/BMP-2 in GelMA, and BMP-2 in OMA/GelMA coacervate hydrogels at days 0, 7, 14, 21 and 28. Photoencapsulated hMSCs in the coacervate hydrogels were cultured in osteogenic differentiation media at 37° C. with 5% $CO_2$. The scale bars indicate 100 μm. (B) A graph showing quantification of DNA in the constructs at days 7, 14, 21, 28, 42, 56 and 112. *p<0.05 compared with BMP-2 in the hydrogel groups at a specific time point.
Figure 6B:
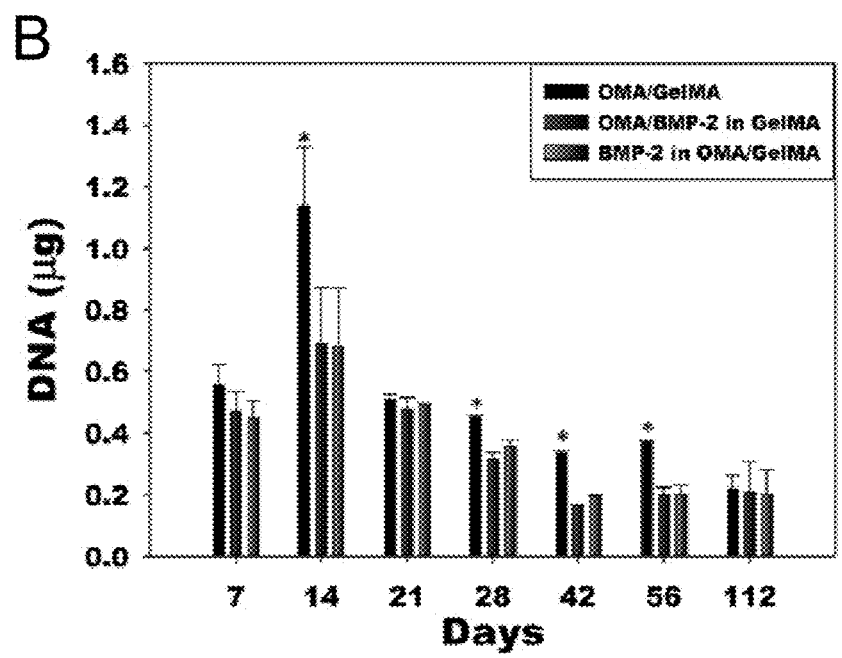

This OMA/GelMA coacervation systems exhibit microdroplet formation in OMA equilibrium phase, which can be further photocrosslinked in the presence of low level UV light and a photoinitiator to form a hydrogel. Microspheres containing bioactive molecules can be easily incorporated and homogenously distributed within the hydrogel through this coacervation approach for localized delivery and exposure of these molecules in a controlled and sustained manner over time to cells incorporated in the microspheres, in the equilibrium phase of the hydrogel and/or surrounding the hydrogel (FIG. 11A). To investigate whether incorporating human bone morphogenetic protein-2 (BMP-2) into the GelMA solution, which mainly comprised the resulting coacervate microdroplets, could delay the release of the growth factor, compared to BMP-2 in the OMA solution, the release profiles of BMP-2 from two different coacervate-laden hydrogel systems were measured (FIG. 11B). The growth factor release from OMA/GelMA coacervate hydrogels when BMP-2 was originally in the OMA solution (red triangles) was more rapid than release from coacervates formed with BMP-2 originally in the GelMA solution (black circles). The release of BMP-2 could be further delayer by the addition of photocrosslinkable heparin into the coacervate hydrogels due to affinity binding between heparin and the growth factor (FIG. 5). The affinity interactions result from electrostatic interactions between the negatively charged sulfate groups of heparin and the positively charged amino acid groups of the growth factor.

To investigate the effect of prolonged presentation of BMP-2 on the osteogenic differentiation of stem cells in this system, human mesenchymal stem cells (hMSCs) were photoencapsulated in OMA/GelMA coacervate hydrogels and cultured in osteogenic differentiation media. As shown in FIGS. 11C-E and FIG. 6 high cell viability was observed throughout all groups for 4 weeks, indicating the mixing and photoencapsulation process, macromers, and the OMA/GelMA coacervate hydrogels themselves and their degradation products are cytocompatible. Cell/hydrogel constructs were evaluated for hMSC osteogenic differentiation by measuring alkaline phosphatase (ALP) activity, which is an early osteogenic differentiation marker, determining relative mRNA expression of Runt-related transcription factor 2 (Runx2), which is one of the earlier and most specific osteogenic differentiation makers, and bone sialoprotein (BSP), which is a later osteogenic differentiation marker, staining for calcium using Alizarin red S, and quantifying calcium deposition. Compared to the OMA/GelMA group without BMP-2, the ALP activity of photoencapsulated hMSCs could more rapidly increase by BMP-2 delivery from the coacervate or equilibrium phase by day 28, and then gradually decreased (FIG. 11F). When the BMP-2 was delivered from the coacervate phase, photoencapsulated hMSCs showed significantly higher ALP activity at day 28, compared to BMP-2 delivered form equilibrium phase, and maximal ALP activity over the duration of the experiment was quantified for both of these conditions at this time point. A quantitative analysis of mRNA expression levels of Runx2 and BSP were evaluated by real-time quantitative reverse transcription-polymerase chain reaction (qRT-PCR) (FIGS. 11G-H). Compared to the control group without BMP-2, hMSCs expressed significantly higher Runx2 by BMP-2 delivery from coacervate or equilibrium phase at day 14 (FIG. 11G). In addition, Runx2 expression level of hMSCs in the OMA/BMP-2 in GelMA group was also significantly higher than that of the control group by day 28. Photoencapsulated hMSCs expressed significantly higher BSP when BMP-2 was delivered from the coacervate hydrogels compared to the controls at day 28, while there was no significant difference among any groups at day 14 (FIG. 11H).

Figure 7:
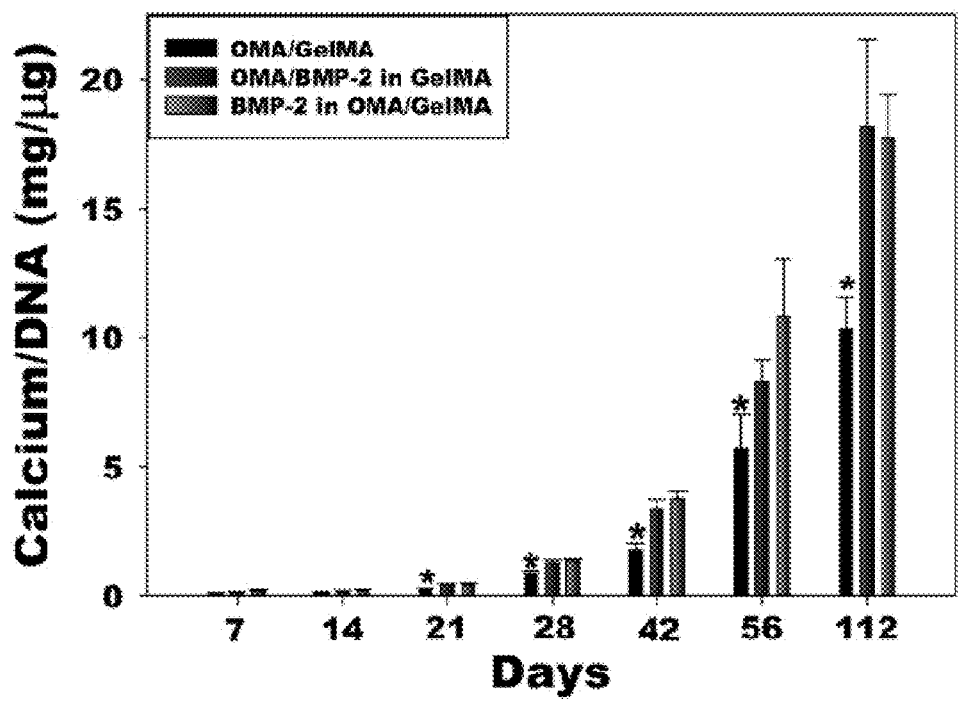
FIG. 7 illustrates a graph showing quantification of calcium content (N=6) in the heparin-modified constructs. All quantitative data is expressed as mean±standard deviation. Statistical analysis was performed with one-way analysis of variance (ANOVA) with Tukey significant difference post hoc test using Origin software. *p<0.05 compared with BMP-2 in OMA/GelMA and OMA/BMP-2 in GelMA groups at a specific time point.

Since mineralization is the ultimate indicator of stem cell osteogenic differentiation, the calcium deposition in the hMSC/hydrogel constructs was then visualized and quantified by Alizarin red staining and a calcium assay, respectively. Compared to the control group, more intense Alizarin red staining was observed in the BMP-2 delivery groups at days 28 and 56 (FIGS. 11I-J). Moreover, the intensity of the staining signal was greatest when the BMP-2 was loaded in the coacervate phase. As shown in FIG. 11K, similar to the Alizarin red staining results, calcium deposition was significantly higher up to day 112 in coacervate hydrogels groups delivering BMP-2 compared to the control group, with the highest calcium deposition in the OMA/BMP-2 in GelMA hydrogels likely due to BMP-2 presentation in the hydrogels for a longer period of time. As shown in FIG. 7, heparin modification of coacervate hydrogels further enhanced the calcium deposition in the coacervate hydrogels. These results demonstrate that long-term presentation of bioactive BMP-2 in the coacervate hydrogels enhances osteogenic differentiation of photoencapsulated stem cells and bone-related mineralization of the extracellular environment.

Micro- or nanoparticle-incorporated hydrogels have been widely studied to achieve sustained localized delivery of bioactive molecules for tissue engineering applications such as regenerating bone or cartilage. Localized and controlled spatial and temporal presentation of these bioactive molecule have been demonstrated to be valuable in regulating encapsulated cell behavior in such tissue engineering strategies. However, in these systems, it can be technically challenging to fabricate the micro- or nanoparticles with encapsulated bioactive molecules without loss of their bioactivity due to use of organic solvents, high temperatures and/or shear stress. In this example, a system has been successfully engineered for the spontaneous formation of coacervates and/or coacervate-laden photocrosslinked hydrogels derived from the simple mixing of OMA and GelMA in aqueous solutions at physiological conditions for long-term localized delivery of growth factor. We demonstrated that the resultant compartments could be utilized as a novel platform for localized, sustained bioactive molecule delivery to encapsulated stem cells for therapeutic applications like bone tissue engineering. In addition to delivery of a single growth factor, particle-based systems have also been implemented to present multiple growth factors, such as BMP-2 and BMP-7, BMP-2 and insulin-like growth factor, vascular endothelial growth factor (VEGF) and BMP-2, and VEGF and platelet-derived growth factor (PDGF), to drive and enhance biologic processes such as osteogenesis and angiogenesis. The coacervate system presented here exhibited differential release profiles of a single growth factor depending on whether heparin was used in the system and whether the growth factor was within the coacervate microdroplets or the surrounding equilibrium phase. Thus, the OMA/GelMA coacervate microdroplet-embedded hydrogel platform could be utilized for the regulated spatiotemporal presentation of multiple growth factors from the same system, which could synergistically enhance tissue regeneration.

In summary, the spontaneous formation of coacervate microdroplets and/or coacervate-laden photocrosslinked hydrogels derived from the simple mixing of photocrosslinkable OMA and GelMA over a wide pH range at room temperature has been demonstrated. This system enables simultaneous creation of drug-laden microdroplets and encapsulation of stem cells in photopolymerized coacervate hydrogels under physiological conditions and can be utilized as a novel platform for in situ formation of localized, sustained bioactive molecule delivery to encapsulated stem cells for therapeutic applications.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A composition comprising:
   a plurality of coacervate microdroplets and/or nanodroplets that include an oxidized alginate and a methacrylated gelatin, and at least one bioactive agent incorporated in the plurality of coacervate microdroplets and/or nanodroplets, wherein the oxidized alginate has an oxidation percentage of at least 10% of uronic acid units of alginate and the methacrylated gelatin has a methacrylation percentage of about 10% to about 99% of amine groups of gelatin.

2. The composition of claim 1, wherein the oxidized alginate has an oxidation percentage up to 50% of uronic acid units of alginate.

3. The composition of claim 2, wherein the oxidized alginate is methacrylated and has a methacrylation percentage up to 45% of alginate carboxylic acid reactive groups.

4. The composition of claim 1, further comprising a cytocompatible hydrogel matrix in which the coacervate microdroplets and/or nanodroplets are suspended.

5. The composition of claim 4, wherein the hydrogel matrix is cross-linked.

6. The composition of claim 4, wherein the hydrogel matrix includes a plurality of cells and the plurality of coacervate microdroplets and/or nanodroplets provide controlled release of the bioactive agent to the plurality of cells.

7. The composition of claim 6, wherein the bioactive agent comprises BMP-2 and the cells comprise progenitor cells.

8. The composition of claim 4, wherein the hydrogel further includes photocrosslinkable heparin.

9. A coacervate hydrogel comprising:
crosslinked oxidized alginate and methacrylated gelatin that form a hydrogel matrix and a plurality of coacervate microdroplets and/or nanodroplets suspended in the matrix, wherein the oxidized alginate has an oxidation percentage of at least 10% of uronic acid units of alginate and the methacrylated gelatin has a methacrylation percentage of about 10% to about 99% of amine groups of gelatin.

10. The hydrogel of claim 9, wherein at least one bioactive agent is incorporated in the coacervate microdroplets and/or nanodroplets and/or matrix.

11. The hydrogel of claim 9, wherein the oxidized alginate has an oxidation percentage up to 50% of uronic acid units of alginate.

12. The hydrogel of claim 10, wherein the oxidized alginate is methacrylated and has a methacrylation percentage up to 45% of alginate carboxylic acid reactive groups.

13. The hydrogel of claim 10, wherein the hydrogel matrix includes a plurality of cells and the plurality of coacervate microdroplets and/or nanodroplets provide controlled release of the bioactive agent to the plurality of cells.

14. The hydrogel of claim 13, wherein the bioactive agent comprises BMP-2 and the cells comprise hMSCs.

15. A coacervate hydrogel comprising:
a crosslinked oxidized methacrylated alginate and a methacrylated gelatin that form a hydrogel matrix and a plurality of coacervate microdroplets and/or nanodroplets, wherein the oxidized methacrylated alginate has an oxidation percentage of 10% up to 50% of uronic acid units and a methacrylation percentage up to 45% of carboxylic acid reactive groups of alginate, the methacrylated gelatin has a methacrylation percentage of at least about 10% to about 99% of amine groups of alginate.

16. The hydrogel of claim 15, further comprising at least one bioactive agent incorporated in the microdroplets and/or nanodroplets and/or matrix.

17. The hydrogel of claim 16, wherein the hydrogel matrix includes a plurality of cells and the plurality of coacervate microdroplets and/or nanodroplets provide controlled release of the bioactive agent to the plurality of cells.

18. The hydrogel of claim 17, wherein the bioactive agent comprises BMP-2 and the cells comprise hMSCs.

* * * * *